United States Patent
DeCillis et al.

(10) Patent No.: US 10,328,069 B2
(45) Date of Patent: Jun. 25, 2019

(54) PHOSPHATIDYLINOSITOL 3-KINASE INHIBITORS FOR THE TREATMENT OF LYMPHOPROLIFERATIVE MALIGNANCIES

(71) Applicants: Exelixis, Inc., South San Francisco, CA (US); Sanofi, Paris (FR)

(72) Inventors: Arthur DeCillis, Madison, CT (US); Joanne Lager, Hollis, NH (US)

(73) Assignee: EXELIXIS, INC., Alameda, CA (US)

( * ) Notice: Subject to any disclaimer, the term of this patent is extended or adjusted under 35 U.S.C. 154(b) by 0 days.

(21) Appl. No.: 15/600,147

(22) Filed: May 19, 2017

(65) Prior Publication Data

US 2017/0296529 A1    Oct. 19, 2017

Related U.S. Application Data

(63) Continuation of application No. 14/355,775, filed as application No. PCT/US2012/062999 on Nov. 1, 2012, now abandoned.

(60) Provisional application No. 61/568,189, filed on Dec. 8, 2011, provisional application No. 61/553,990, filed on Nov. 1, 2011.

(51) Int. Cl.
| | |
|---|---|
| *A61K 31/498* | (2006.01) |
| *A61K 31/47* | (2006.01) |
| *C07D 241/44* | (2006.01) |
| *C07D 215/233* | (2006.01) |

(52) U.S. Cl.
CPC ............ *A61K 31/47* (2013.01); *A61K 31/498* (2013.01); *C07D 215/233* (2013.01); *C07D 241/44* (2013.01)

(58) Field of Classification Search
CPC .......................... C07D 241/44; A61K 31/498
See application file for complete search history.

(56) References Cited

U.S. PATENT DOCUMENTS

| | | | |
|---|---|---|---|
| 7,989,622 B2 | 8/2011 | Bajjalieh et al. | |
| 8,044,062 B2 | 10/2011 | Baik et al. | |
| 8,481,001 B2 | 7/2013 | Aftab et al. | |
| 8,637,499 B2 | 1/2014 | Aay et al. | |
| 8,642,584 B2 | 2/2014 | Aftab et al. | |
| 8,901,137 B2 | 12/2014 | Aftab et al. | |
| 9,011,863 B2 | 4/2015 | Lamb et al. | |
| 9,346,807 B2 | 5/2016 | Kearney | |
| 9,364,475 B2* | 6/2016 | Parikh | A61K 9/2054 |
| 9,670,212 B2 | 6/2017 | Leahy | |
| 10,035,790 B2 | 7/2018 | Xu | |
| 10,053,470 B2 | 8/2018 | Leahy | |
| 2009/0062274 A1 | 3/2009 | Baik et al. | |
| 2009/0181963 A1* | 7/2009 | Dehnhardt | C07D 487/04 514/234.2 |
| 2009/0270430 A1 | 10/2009 | Baik et al. | |
| 2010/0075947 A1 | 3/2010 | Aftab et al. | |
| 2010/0087456 A1 | 4/2010 | Baik et al. | |
| 2010/0150827 A1 | 6/2010 | Buhr et al. | |
| 2010/0087440 A1 | 8/2010 | Bajjalieh et al. | |
| 2010/0209340 A1 | 8/2010 | Buhr et al. | |
| 2010/0209420 A1 | 8/2010 | Lamb et al. | |
| 2010/0298290 A1 | 11/2010 | Anand et al. | |
| 2011/0123434 A1 | 5/2011 | Lamb et al. | |
| 2011/0207712 A1 | 8/2011 | Bajjalieh et al. | |
| 2011/0237608 A1 | 9/2011 | Baik et al. | |
| 2012/0134959 A1* | 5/2012 | Curran | C07D 498/08 424/85.6 |
| 2013/0343988 A1 | 12/2013 | Buhr et al. | |
| 2014/0005172 A1 | 1/2014 | Rice | |
| 2014/0018347 A1 | 1/2014 | Rice | |
| 2014/0066431 A1 | 3/2014 | Rice et al. | |
| 2014/0073628 A1 | 3/2014 | Rice | |
| 2014/0080810 A1 | 3/2014 | Rice et al. | |
| 2014/0100215 A1 | 4/2014 | Aftab et al. | |

(Continued)

FOREIGN PATENT DOCUMENTS

| | | |
|---|---|---|
| WO | 2008127594 | 10/2008 |
| WO | 2009017838 | 2/2009 |
| WO | 2012065057 | 5/2012 |

OTHER PUBLICATIONS

Sharman et al. Blood, Nov. 2011, vol. 118, No. 21, Abstract No. 1787 (Year: 2011).*

(Continued)

*Primary Examiner* — James D. Anderson
(74) *Attorney, Agent, or Firm* — Honigman LLP; Heidi M. Berven; Jonathan P. O'Brien

(57) ABSTRACT

Methods are provided for treating a lymphoproliferative malignancy to a patient in need of such treatment, comprising administering to the patient an effective amount of compound A as described herein.

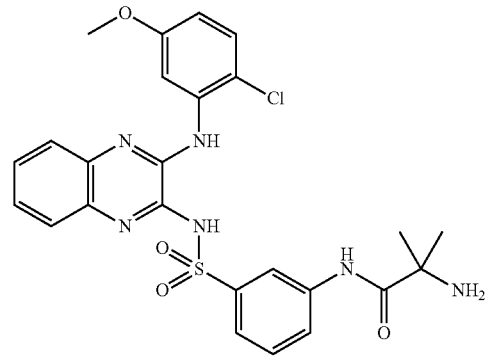

5 Claims, 2 Drawing Sheets

(56) References Cited

U.S. PATENT DOCUMENTS

| | | |
|---|---|---|
| 2014/0107100 A1 | 4/2014 | Rice et al. |
| 2014/0154232 A1* | 6/2014 | Serrano Marugan .. A61K 31/35 |
| | | 424/94.6 |
| 2014/0296265 A1 | 10/2014 | DeCillis et al. |
| 2014/0302012 A1 | 10/2014 | DeCillis et al. |
| 2014/0303172 A1 | 10/2014 | DeCillis et al. |
| 2014/0378436 A9 | 12/2014 | Rice |

OTHER PUBLICATIONS

Burris et al, Journal of Clinical Oncology, May 20, 2010, vol. 28, No. 15, Suppl., Abstract #3005.
Edelman et al., Journal of Clinical Oncology, May 20, 2010, vol. 28, No. 15, Suppl., Abstract #3004.
International Search Report for PCT/US2012/062999, dated Feb. 27, 2013.
Traynor et al., Journal of Clinical Oncology, May 20, 2010, vol. 28, No. 15, Suppl., Abstract #3078.

* cited by examiner

PHOSPHATIDYLINOSITOL 3-KINASE INHIBITORS FOR THE TREATMENT OF LYMPHOPROLIFERATIVE MALIGNANCIES

CROSS-REFERENCE TO RELATED APPLICATIONS

This application is a continuation application of U.S. Ser. No. 14/355,775, filed May 1, 2014, which claims priority under 35 U.S.C. § 371 to Patent Cooperation Treaty application PCT/US2012/062999, filed Nov. 1, 2012, which claims the benefit of U.S. provisional application No. 61/568,189, filed Dec. 8, 2011, and U.S. provisional application No. 61/553,990, filed Nov. 1, 2011, the entire contents of which are incorporated herein by reference.

BACKGROUND

Lymphoproliferative malignancies, including lymphomas and lymphocytic leukemia, are common malignancies with an incidence of approximately 93,000 new cases a year in the United States.

Treatment modalities being developed to treat these malignancies are being met with varying levels of success. For example, among the more than 30 subtypes of non-Hodgkin lymphoma (NHL), mantle cell lymphoma (MCL) accounts for 3 percent to 10 percent of cases. MCL can be treated at diagnosis or recurrence with various chemotherapeutic regimens. Although the prognosis is improving given these advances in treatment, the median overall survival remains 4.8 years.

Follicular lymphoma (FL) is a common indolent B-cell NHL that constitutes approximately 20 percent of all newly diagnosed lymphoma cases and approximately 70 percent of all indolent NHL. Like many lymphomas, it is increasing in incidence, with over 24,000 new cases diagnosed each year. While there is an increasing number of available treatment modalities for FL, including radioimmunotherapy alone or in combination with chemotherapy, as well as bone marrow transplantation, many FL patients develop treatment-refractory disease or relapse due to molecular escape mechanisms.

B-cell chronic lymphocytic leukemia (CLL) is the most common type of adult leukemia in the United States, with approximately 15,000 new cases each year. According to the World Health Organization (WHO) classification, CLL is identical (i.e., one disease at different stages) to the mature peripheral B-cell neoplasm small lymphocytic lymphoma (SLL). In spite of various treatment options, CLL/advanced SLL is a progressive disease and once symptomatic, patients have a relatively short overall survival, ranging from 18 months to 6 years, with a 22.5 percent 10-year survival expectation.

As a result, there is an ongoing need for clinically effective agents for treating lymphoproliferative malignancies, including chronic lymphocytic leukemia/small lymphocytic lymphoma, Hodgkin's lymphoma, Waldenstrom's macroglobulinemia, follicular lymphoma, or diffuse large B-cell lymphoma or transformed lymphoma.

SUMMARY

Accordingly, in one aspect, methods for treating lymphoproliferative disorders are provided, comprising administering to a patient in need of such treatment a therapeutically effective amount of a Compound of Formula Ia

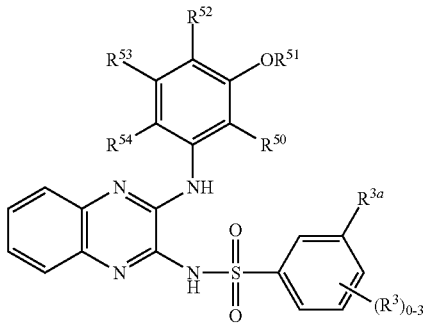

or a pharmaceutically acceptable salt thereof, wherein:

$R^{50}$ is hydrogen;

$R^{51}$ is methyl;

$R^{52}$ is hydrogen;

$R^{53}$ is hydrogen or alkoxy; and $R^{54}$ is hydrogen, alkyl, alkoxy, or halo; or $R^{53}$ and $R^{54}$ together with the carbons to which they are attached form a 6-membered heteroaryl; and $R^3$ is halo or methyl; and $R^{3a}$ is $-N(R^7)C(O)-C_1-C^6$-alkylene-$N(R^{7a})(R^{7b})$ where $R^7$ is hydrogen and $R^{7a}$ and $R^{7b}$ are independently hydrogen, alkyl, aminoalkyl, alkylaminoalkyl, or dialkylaminoalkyl;

In another embodiment, the method comprises administering to the patient an effective amount of Compound A:

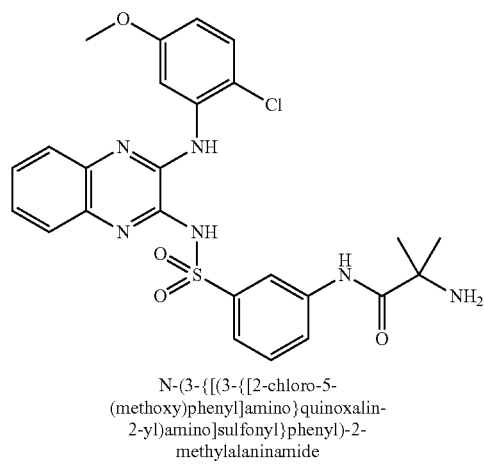 [SMILES: COc1ccc(Cl)c(Nc2nc3ccccc3nc2NS(=O)(=O)c2cccc(NC(=O)C(C)(C)N)c2)c1]

N-(3-{[(3-{[2-chloro-5-(methoxy)phenyl]amino}quinoxalin-2-yl)amino]sulfonyl}phenyl)-2-methylalaninamide or a tautomer, zwitterion, or pharmaceutically salt thereof.

In another embodiment, Compound A is administered as a pharmaceutical composition.

Other objects, features and advantages will become apparent from the following detailed description. The detailed description and specific examples are given for illustration only since various changes and modifications within the spirit and scope of the invention will become apparent to those skilled in the art from this detailed description. Further, the examples demonstrate the principle of the invention and cannot be expected to specifically illustrate the application of this invention to all the examples where it will be obviously useful to those skilled in the prior art.

DETAILED DESCRIPTION

Abbreviations and Definitions

Figure 1:
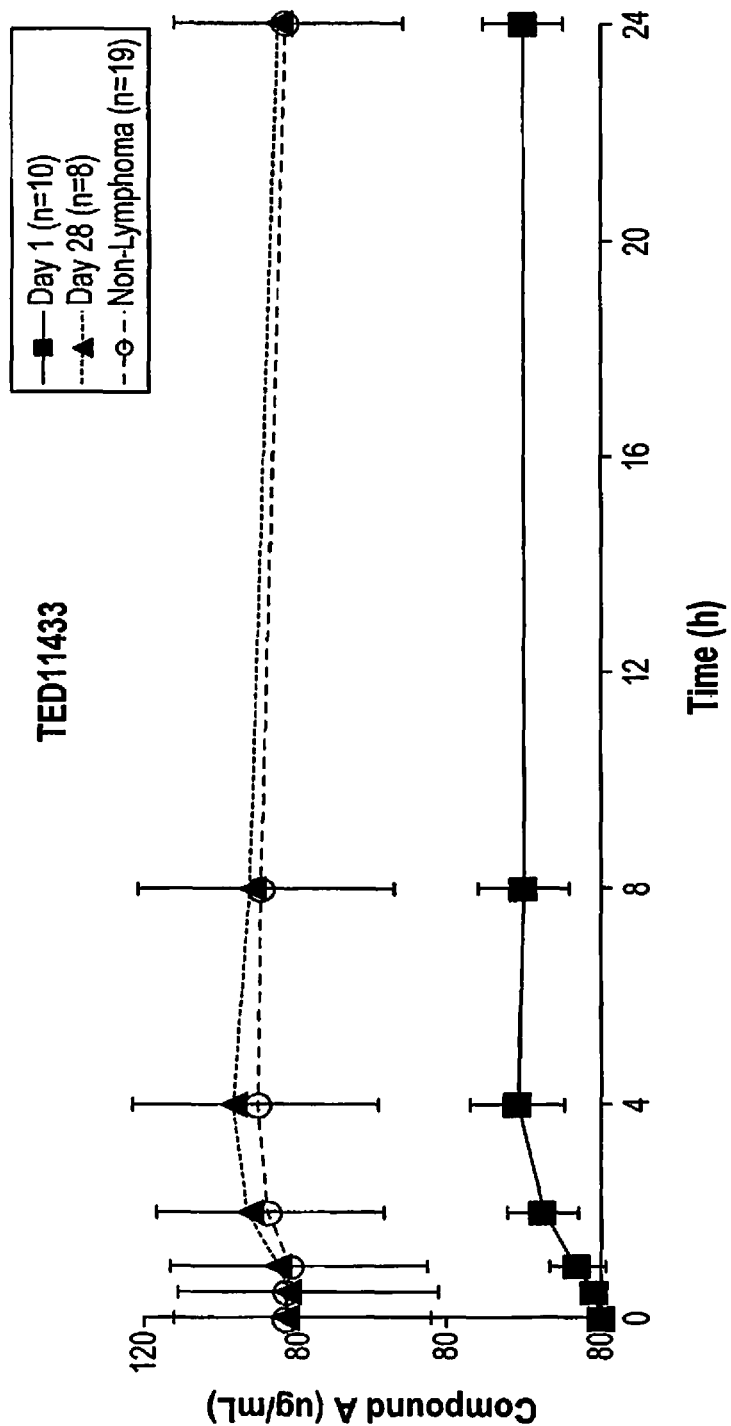
FIG. 1 depicts the plasma pharmacokinetics observed for Compound A.
Figure 2:
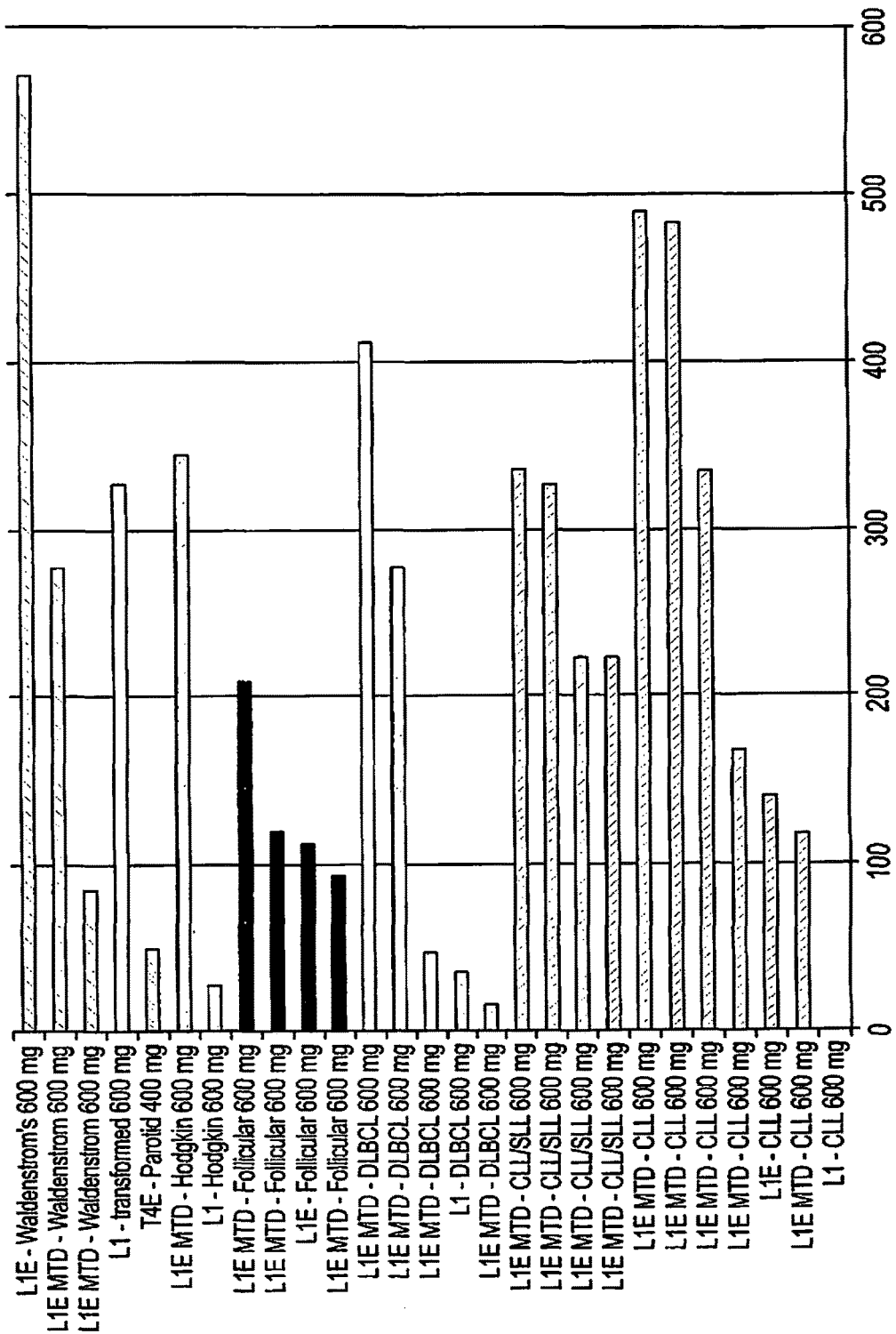
FIG. 2 summarizes the results of a clinical study in patients with lymphoma.

The following abbreviations and terms have the indicated meanings throughout:

| Abbreviation | Meaning |
| --- | --- |
| Ac | acetyl |
| br | broad |
| ° C. | degrees Celsius |
| c- | cyclo |
| CBZ | CarboBenZoxy = benzyloxycarbonyl |
| d | doublet |
| dd | doublet of doublet |
| dt | doublet of triplet |
| DCM | dichloromethane |
| DMA | Dimethylacetamide |
| DME | 1,2-dimethoxyethane |
| DMF | N,N-dimethylformamide |
| DMSO | dimethyl sulfoxide |
| dppf | 1,1'-bis(diphenylphosphano)ferrocene |
| EI | Electron Impact ionization |
| g | gram(s) |
| h or hr | hour(s) |
| HPLC | high pressure liquid chromatography |
| L | liter(s) |
| M | molar or molarity |
| m | Multiplet |
| mg | milligram(s) |
| MHz | megahertz (frequency) |
| Min | minute(s) |
| mL | milliliter(s) |
| μL | microliter(s) |
| μM | Micromole(s) or micromolar |
| mM | Millimolar |
| mmol | millimole(s) |
| mol | mole(s) |
| MS | mass spectral analysis |
| N | normal or normality |
| nM | Nanomolar |
| NMR | nuclear magnetic resonance spectroscopy |
| q | Quartet |
| RT | Room temperature |
| s | Singlet |
| t or tr | Triplet |
| TFA | trifluoroacetic acid |
| THF | tetrahydrofuran |
| TLC | thin layer chromatography |

The symbol "—" means a single bond, "=" means a double bond, "≡" means a triple bond, "====" means a single or double bond. The symbol "⌇" refers to a group on a double-bond as occupying either position on the terminus of a double bond to which the symbol is attached; that is, the geometry, E- or Z-, of the double bond is ambiguous. When a group is depicted removed from its parent formula, the "∼" or "—|" symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —$CH_2CH_2$—. It is understood by one of ordinary skill in the art that the aforementioned descriptive techniques are common in the chemical arts to provide brevity and simplicity to description of otherwise complex structures.

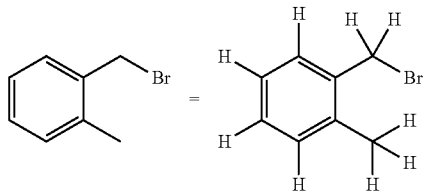

If a group "R" is depicted as "floating" on a ring system, as for example in the formula:

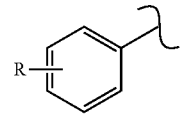

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

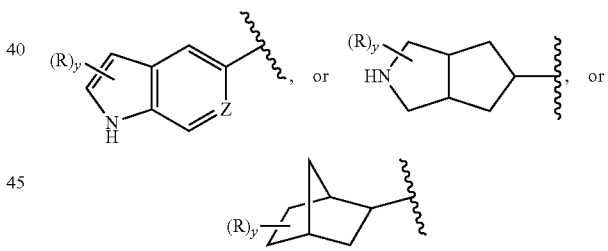

then, unless otherwise defined, a substituent "R" may reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "Z" equals =CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When a group "R" is depicted as existing on a ring system containing saturated carbons, as for example in the formula:

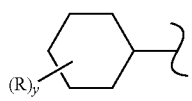

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

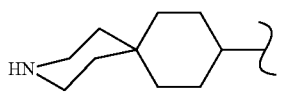

"Administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents, "administration" and its variants are each understood to include concurrent and sequential introduction of the compound or prodrug thereof and other agents.

"Alkoxy" means an -OR group where R is alkyl group as defined herein. Examples include methoxy, ethoxy, propoxy, isopropoxy, and the like.

"Alkyl" means a linear saturated monovalent hydrocarbon radical of one to six carbon atoms or a branched saturated monovalent hydrocarbon radical of three to 6 carbon atoms, e.g., methyl, ethyl, propyl, 2-propyl, butyl (including all isomeric forms), or pentyl (including all isomeric forms), and the like.

"Alkylamino" means a —NHR group where R is alkyl, as defined herein.

"Alkylaminoalkyl" means an alkyl group substituted with one or two alkylamino groups, as defined herein.

"Amino" means —NH$_2$.

"Aminoalkyl" means an alkyl group substituted with at least one, specifically one, two or three, amino groups.

"Aryl" means a monovalent six- to fourteen-membered, mono- or bi-carbocyclic ring, wherein the monocyclic ring is aromatic and at least one of the rings in the bicyclic ring is aromatic. Unless stated otherwise, the valency of the group may be located on any atom of any ring within the radical, valency rules permitting. Representative examples include phenyl, naphthyl, and indanyl, and the like.

"Dialkylamino" means a —NRR' radical where R and R' are alkyl as defined herein, or an N-oxide derivative, or a protected derivative thereof, e.g., dimethylamino, diethylamino, N,N-methylpropylamino or N,N-methylethylamino, and the like.

"Dialkylaminoalkyl" means an alkyl group substituted with one or two dialkylamino groups, as defined herein.

"Halogen" or "halo" refers to fluorine, chlorine, bromine or iodine.

"Haloalkoxy" means an —OR' group where R' is haloalkyl as defined herein, e.g., trifluoromethoxy or 2,2,2-trifluoroethoxy, and the like.

"Heteroaryl" means a monocyclic, fused bicyclic, or fused tricyclic, monovalent radical of 5 to 14 ring atoms containing one or more, specifically one, two, three, or four ring heteroatoms independently selected from —O—, —S(O)$_N$— (n is 0, 1, or 2), —N—, —N(R$^x$)—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. R$^x$ is hydrogen, alkyl, hydroxy, alkoxy, acyl, or alkylsulfonyl. Fused bicyclic radical includes bridged ring systems. Unless stated otherwise, the valency may be located on any atom of any ring of the heteroaryl group, valency rules permitting. When the point of valency is located on the nitrogen, R$^x$ is absent. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, isothiazolyl, thiadiazolyl, benzothiazolyl, benzothienyl, and the derivatives thereof, or N-oxide or a protected derivative thereof.

"Heteroatom" refers to O, S, N, or P.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted arylC$_{1-8}$ alkyl," optional substitution may occur on both the "C$_{1-8}$ alkyl" portion and the "aryl" portion of the molecule may or may not be substituted. A list of exemplary optional substitutions is presented below in the definition of "substituted."

"Pharmaceutical composition" comprises 1) a Compound of Formula I or a single isomer thereof where the compound is optionally as a pharmaceutically acceptable salt and additionally optionally as a hydrate and additionally optionally as a solvate thereof; and 2) a pharmaceutically acceptable carrier, excipient, or diluent.

As used herein, "Compound A," which is a compound of Formula I and of Formula Ia, has the following structure

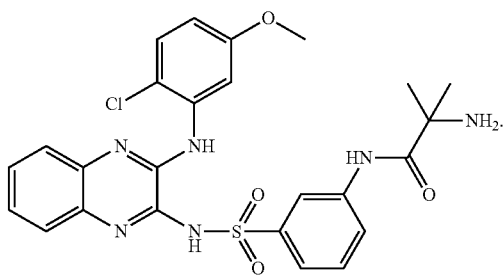 [SMILES: COc1ccc(Cl)c(Nc2nc3ccccc3nc2NS(=O)(=O)c2cccc(NC(=O)C(C)(C)N)c2)c1]

Compound A is known by its chemical name N-(3-{[(3-{[2-chloro-5-(methoxy)phenyl]amino}quinoxalin-2-yl)amino]sulfonyl}phenyl)-2-methylalaninamide. As discussed in more detail below, the compound may exist in several tautomeric or zwitterionic forms. Accordingly, as used herein the terms "Compound A" and "N-(3-{[(3-{[2-chloro-5-(methoxy)phenyl]amino}quinoxalin-2-yl)amino]sulfonyl}phenyl)-2-methylalaninamide" encompass all possible tautomeric and zwitterionic forms of the compound.

"Yield" for each of the reactions described herein is expressed as a percentage of the theoretical yield.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

The terms "effective amount" or "pharmaceutically effective amount" or "therapeutically effective amount" refer to a sufficient amount of an agent to provide the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In reference to cancer, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations. The effective amount of the drug or composition may: (i) reduce the number of cancer cells; (ii) reduce tumor size; (iii) inhibit, retard, slow to some extent, and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. In one example, an "effective amount" is the amount of Compound A or a pharmaceutically acceptable salt thereof clinically proven to effect a significant decrease in or slowing of progression of lymphoproliferative malignancies A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Preferable salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

Unless otherwise indicated, "treating" or "treatment" of a disease, disorder, or syndrome, as used herein, means inhibiting the disease, disorder, or syndrome, that is, arresting its development; and relieving the disease, disorder, or syndrome, that is, causing regression of the disease, disorder, or syndrome. As is known in the art, in the context of treatment, adjustments for systemic versus localized delivery, age, body weight, general health, sex, diet, time of administration, drug interaction and the severity of the condition may be necessary, and will be ascertainable with routine experimentation by one of ordinary skill in the art.

"Prevention" means preventing the disease, disorder, or syndrome from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome.

As used herein, the term "about" generally indicates a possible variation of no more than 10%, 5%, or 1% of a value. For example, "about 25 mg/kg" will generally indicate, in its broadest sense, a value of 22.5-27.5 mg/kg, i.e., 25±10 mg/kg.

Embodiments

The following paragraphs present a number of embodiments that can be used to practice the invention. In each instance, the embodiment includes both the recited compounds as well as individual isomers and mixtures of isomers. In addition, in each instance, the embodiment includes the pharmaceutically acceptable salts, hydrates, and/or solvates of the recited compounds and any individual isomers or mixture of isomers thereof.

In one embodiment, methods are provided for treating lymphoproliferative malignancies, comprising administering to a patient an effective amount of a Compound of Formula Ia or a pharmaceutical composition comprising a Compound of Formula Ia. In these and other embodiments, the lymphoproliferative malignancies include chronic lymphocytic leukemia/small lymphocytic lymphoma, Hodgkin's lymphoma, Waldenstrom's macroglobulinemia, follicular lymphoma, or diffuse large B-cell lymphoma or transformed lymphoma.

Any of the following embodiments, including the representative compounds described below, may be used to practice any of the methods disclosed herein.

Compounds of Formula Ia

The invention provides a method for treating breast cancer using a compound of Formula I is a compound of Formula Ia:

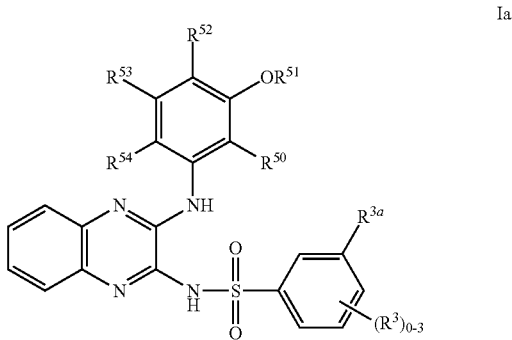

or a pharmaceutically acceptable salt thereof.

In one embodiment of the compound of Formula Ia, $R^{51}$ is methyl; and $R^{50}$, $R^{52}$, and $R^{53}$ are hydrogen and $R^{54}$ is halo or alkoxy or $R^{50}$, $R^{52}$, and $R^{54}$ are hydrogen and $R^{53}$ is alkoxy; or a single stereoisomer or mixture of stereoisomers thereof.

In another embodiment, $R^{3a}$ is —NHC(O)CH$_2$NH(CH$_3$), —NHC(O)CH(CH$_3$)NH$_2$, —NHC(O)C(CH$_3$)$_2$NH$_2$, —NHC(O)—CH1N(CH$_3$)$_2$, —NHC(O)CH$_2$N(CH$_3$)CH$_2$CH$_2$N(CH$_3$)$_2$, —NHC(O)CH(NH$_2$)CH$_2$CH$_3$, —NHC(O)CH$_2$N(CH$_3$)CH$_2$CH$_2$N(CH$_3$)$_2$, or —NHC(O)CH(CH$_3$)NH(CH$_3$).

In another embodiment, the compound of Formula Ia is:

| Structure | Name |
|---|---|
| 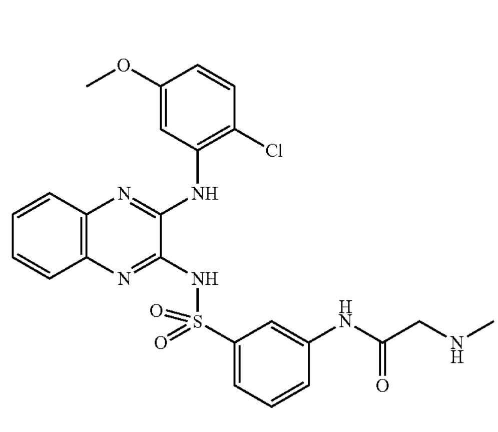 [SMILES: CNCC(=O)Nc1cccc(S(=O)(=O)Nc2nc3ccccc3nc2Nc2cc(OC)ccc2Cl)c1] | N-(3-{[(3-{[2-chloro-5-(methoxy)phenyl]amino}quinoxalin-2-yl)amino]sulfonyl}-phenyl)-N-2-methylglycinamide |

| Structure | Name |
|---|---|
| 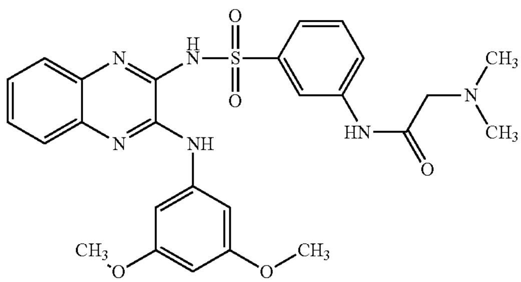 [SMILES: COc1cc(Nc2nc3ccccc3nc2NS(=O)(=O)c2cccc(NC(=O)CN(C)C)c2)cc(OC)c1] | N-(3-{[(3-{[3,5-bis(methoxy)phenyl]amino}quinoxalin-2-yl)amino]sulfonyl}phenyl)-N-2-,N-2-dimethylglycinamide |
| 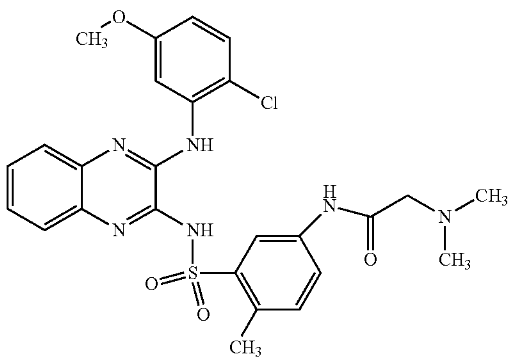 [SMILES: COc1ccc(Cl)c(Nc2nc3ccccc3nc2NS(=O)(=O)c2cc(NC(=O)CN(C)C)ccc2C)c1] | N-(3-{[(3-{[2-chloro-5-(methoxy)phenyl]amino}quinoxalin-2-yl)amino]sulfonyl}-4-methylphenyl)-N-2-,N-2-dimethylglycinamide |
| 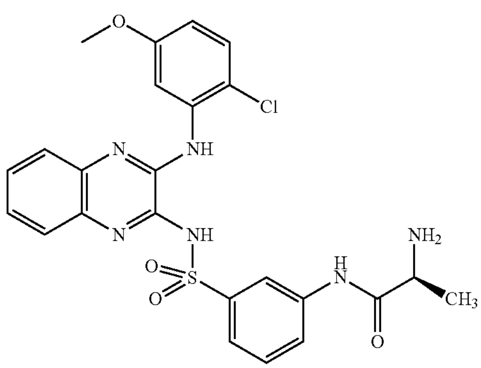 [SMILES: COc1ccc(Cl)c(Nc2nc3ccccc3nc2NS(=O)(=O)c2cccc(NC(=O)[C@H](C)N)c2)c1] | N-(3-{[(3-{[2-chloro-5-(methoxy)phenyl]amino}quinoxalin-2-yl)amino]sulfonyl}phenyl)-L-alaninamide |
| 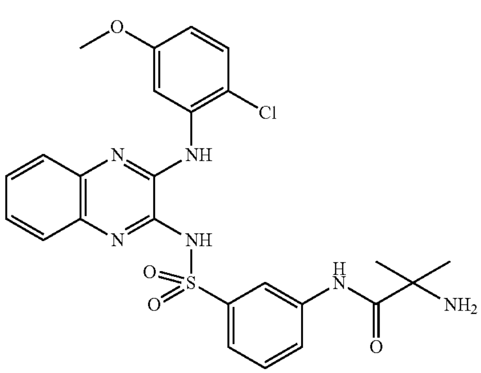 [SMILES: COc1ccc(Cl)c(Nc2nc3ccccc3nc2NS(=O)(=O)c2cccc(NC(=O)C(C)(C)N)c2)c1] | N-(3-{[(3-{[2-chloro-5-(methoxy)phenyl]amino}quinoxalin-2-yl)amino]sulfonyl}phenyl)-2-methylalaninamide |

-continued

| Structure | Name |
|---|---|
| 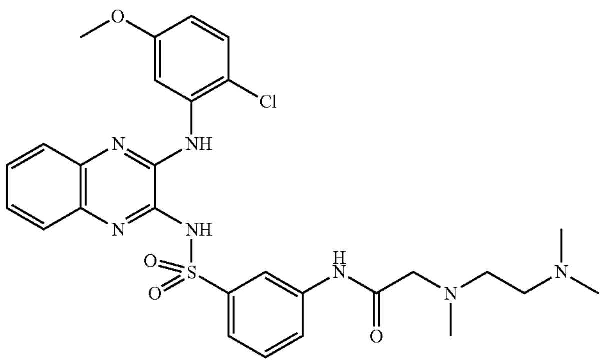 [SMILES: COc1ccc(Cl)c(Nc2nc3ccccc3nc2NS(=O)(=O)c2cccc(NC(=O)CN(C)CCN(C)C)c2)c1] | N-(3-{[(3-{[2-chloro-5-(methoxy)phenyl]amino}quinoxalin-2-yl)amino]sulfonyl}phenyl)-N-2-[2-(dimethylamino)ethyl]-N-2-methylglycinamide |
| 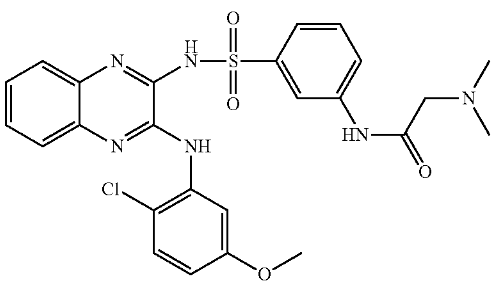 [SMILES: COc1ccc(Cl)c(Nc2nc3ccccc3nc2NS(=O)(=O)c2cccc(NC(=O)CN(C)C)c2)c1] | N-(3-{[(3-{[2-chloro-5-(methoxy)phenyl]amino}quinoxalin-2-yl)amino]sulfonyl}phenyl)-N-2-,N-2-dimethylglycinamide |
| 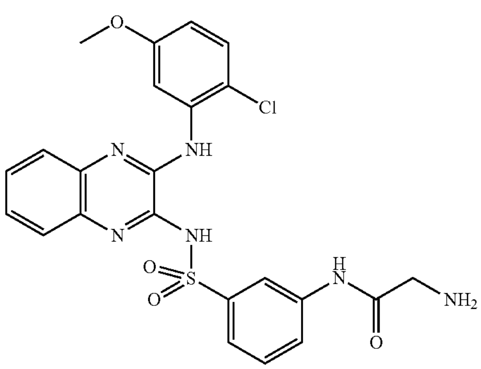 [SMILES: COc1ccc(Cl)c(Nc2nc3ccccc3nc2NS(=O)(=O)c2cccc(NC(=O)CN)c2)c1] | N-(3-{[(3-{[2-chloro-5-(methoxy)phenyl]amino}quinoxalin-2-yl)amino]sulfonyl}phenyl)glycinamide |
| 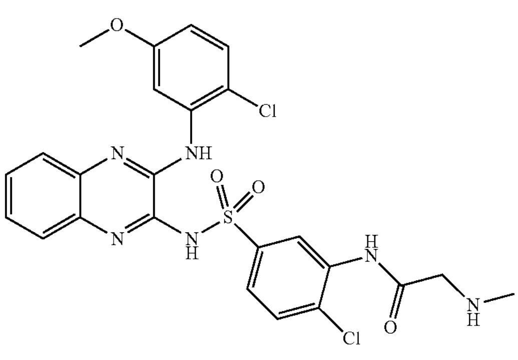 [SMILES: CNCC(=O)Nc1cc(S(=O)(=O)Nc2nc3ccccc3nc2Nc2cc(OC)ccc2Cl)ccc1Cl] | N-(2-chloro-5-{[(3-{[2-chloro-5-(methoxy)phenyl]amino}quinoxalin-2-yl)amino]sulfonyl}phenyl)-N-2-methylglycinamide |

| Structure | Name |
|---|---|
| 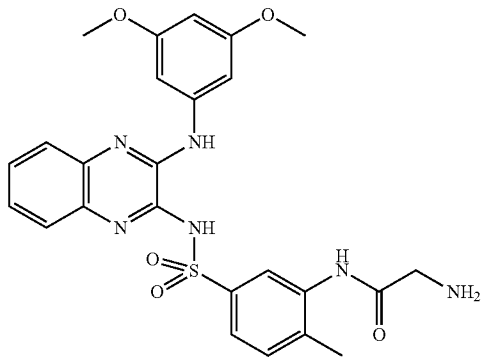 [SMILES: COc1cc(Nc2nc3ccccc3nc2NS(=O)(=O)c2ccc(C)c(NC(=O)CN)c2)cc(OC)c1] | N-(5-{[(3-{[3,5-bis(methoxy)phenyl]amino}quinoxalin-2-yl)amino]sulfonyl}-2-methylphenyl)glycinamide |
| 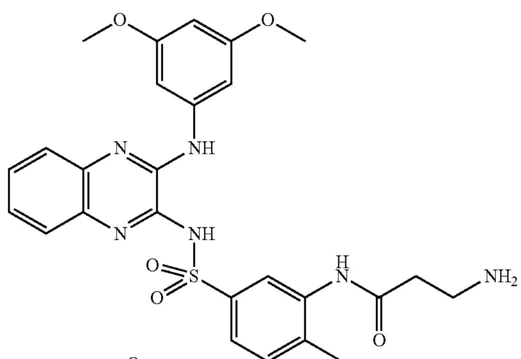 | N-(5-{[(3-{[3,5-bis(methoxy)phenyl]amino}quinoxalin-2-yl)amino]sulfonyl}-2-methylphenyl)-beta-alaninamide |
| | N-(5-{[(3-{[2-chloro-5-(methoxy)phenyl]amino}quinoxalin-2-yl)amino]sulfonyl}-2-methylphenyl)-N-2-,N-2-dimethylglycinamide | or a pharmaceutically acceptable salt thereof.

In another embodiment, the compound of Formula Ia is Compound A:

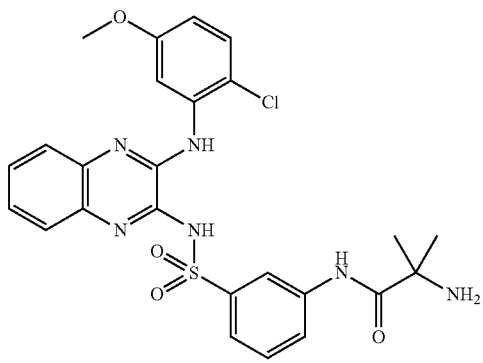

N-(3-{[(3-{[2-chloro-5-me(methoxy)phenyl]amino}quinoxalin-2-yl)amino]sulfonyl}phenyl)-2-methylalaninamide or a tautomer, zwitterion, or pharmaceutically salt thereof.

Additional Embodiments

In one embodiment, the invention provides a method of treating lymphoproliferative malignancies comprising administering to a patient in need of such treatment an effective amount of Compound A.

In another embodiment, Compound A is administered as a 100, 150, or 200 mg capsule.

General Administration

In one aspect, the invention provides pharmaceutical compositions comprising an inhibitor of the PI3Ks of Formula Ia and a pharmaceutically acceptable carrier, excipient, or diluent. In certain other specific embodiments, administration is by the oral route. Administration of the compounds of Formula Ia, or their pharmaceutically acceptable salts, in pure form or in an appropriate pharmaceutical composition, can be carried out via any of the accepted modes of administration or agents for serving similar utilities. Thus, the Compound of Formula Ia can be administered in the same or separate vehicles. Administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, specifically in unit dosage forms suitable for simple administration of precise dosages.

The compositions will include a conventional pharmaceutical carrier or excipient and a Compound of Formula Ia as the/an active agent.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

The choice of formulation depends on various factors such as the mode of drug administration (e.g., for oral administration, formulations in the form of tablets, pills or capsules) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One specific route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Compressed gases may be used to disperse a compound of this invention in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain an effective amount of a compound of the invention, or a pharmaceutically acceptable salt thereof, for treatment of a disease-state in accordance with the teachings of this invention.

In the pharmaceutical compositions disclosed herein, the compounds of Formula I or Ia, or their pharmaceutically acceptable salts or solvates, are administered in an effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of Formula I or Ia can be administered to a patient at dosage levels in the range of about 0.1 to about 1,000 mg per day, or in the range of 50 to 400 mg per day, 100 mg to 800 mg per day, or in the range of 100 mg to 350 mg per day, or in the range of 200 to 700 mg per day, or in the range of 150 mg to 400 mg per day, or in the range of 300 to 600 mg per day.

For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art. If formulated as a fixed dose, such combination products employ the compounds of this invention within the dosage range described above and the other pharmaceutically active agent(s) within approved dosage ranges. Compounds of Formula Ia may alternatively be used sequentially with known pharmaceutically acceptable agent(s) when a combination formulation is inappropriate.

For a normal human adult having a body weight of about 70 kilograms, a dosage in the range of about 0.01 to about 100 mg per kilogram of body weight per day is an example. The specific dosage used for children will generally be lower due to the smaller size and weight of children, and the doses can be adjusted according to size and weight factors, as well as additional factors. For example, the dosage can depend on additional factors including the requirements of the child, the severity of the condition being treated, and the pharmacological activity of the compound being used. The determination of optimum dosages for a particular child is well known to one of ordinary skill in the art. If formulated as a fixed dose, such combination products employ the compounds of this invention within the dosage range described above and the other pharmaceutically active agent(s) within approved dosage ranges. Compounds of Formula Ia may alternatively be used sequentially with known pharmaceutically acceptable agent(s) when a combination formulation is inappropriate.

General Synthesis

Synthesis of Compounds of Formula I

The starting materials and reagents used in preparing these compounds are either available from commercial suppliers such as Aldrich Chemical Co. (Milwaukee, Wis.), or Bache (Torrance, Calif.), or are prepared by methods known to those skilled in the art following procedures set forth in references such as Fisher and Fisher's Reagents for Organic Synthesis, Volumes 1-17 (John Wiley and Sons, 1991); Rod's Chemistry of Carbon Compounds, Volumes 1-5 and Supplemental (Elsevier Science Publishers, 1989); Organic Reactions, Volumes 1-40 (John Wiley and Sons, 1991), March's Advanced Organic Chemistry, (John Wiley and Sons, $4^{th}$ Edition) and Larch's Comprehensive Organic Transformations (VICHY Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure and over a temperature range from about $-78°$o to about $150°$o, in another embodiment from about $0°$o. to about $125°$o and most specifically at about room (or ambient) temperature, e.g., about $20°$o. Unless otherwise stated (as in the case of a hydrogenation), all reactions are performed under an atmosphere of nitrogen.

Prodrugs can be prepared by techniques known to one skilled in the art. These techniques generally modify appropriate functional groups in a given compound. These modified functional groups regenerate original functional groups by routine manipulation or in vivo. Amides and esters of the compounds of the present invention may be prepared according to conventional methods. A thorough discussion of prodrugs is provided in T. Higuchi and V. Stella, "Prodrugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

The compounds of the invention, or their pharmaceutically acceptable salts, may have asymmetric carbon atoms or quaternized nitrogen atoms in their structure. Compounds of Formula I that may be prepared through the syntheses described herein may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

Some of the compounds of the invention may exist as tautomers. For example, where a ketone or aldehyde is present, the molecule may exist in the enol form; where an amide is present, the molecule may exist as the imidic acid; and where an enamine is present, the molecule may exist as an imine. All such tautomers are within the scope of the invention, and to the extent that one structure is used to depict a compound, it includes all such tautomeric forms.

Thus, compounds of Formula I

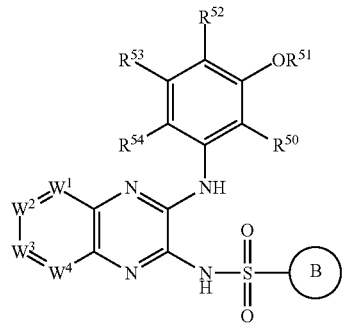

can exist as tautomers. In particular, ring B in the Compound of Formula I or B can be 2-hydroxy-pyridinyl, also described as its structure:

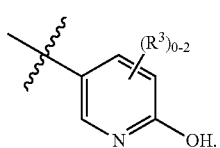

14

Both 2-hydroxy-pyridinyl and the above structure 14 include, and are equivalent to, pyridin-2(1H)-one and its structure 15:

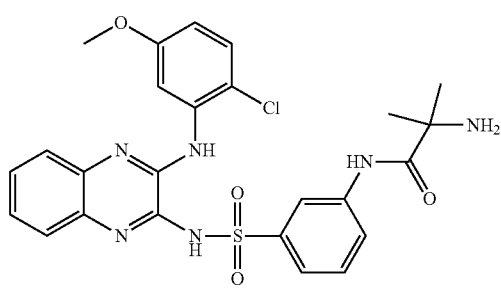

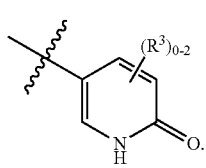

15

Regardless of which structure or which terminology is used, each tautomer is included within the scope of the Invention.

For example, one tautomer of Compound A is Compound A-1:

Compound A-1

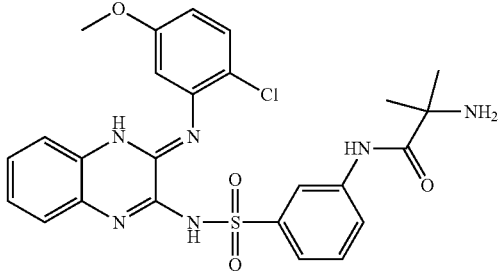

Another tautomer of Compound A is Compound A-2:

Compound A-2

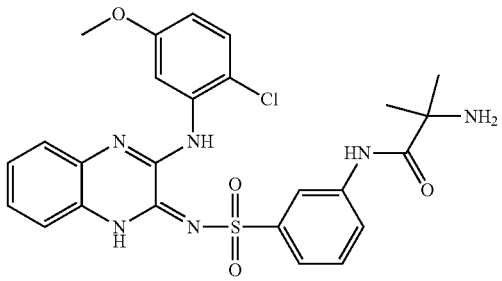

Compound A-2 is named N-(3-{[(2Z)-3-[(2-chloro-5-methoxyphenyl)amino]quinoxalin-2(1H)-ylidene]sulfamoyl}phenyl)-2-methylalaninamide.

As would be understood by a skilled practitioner, tautomeric forms can interconvert.

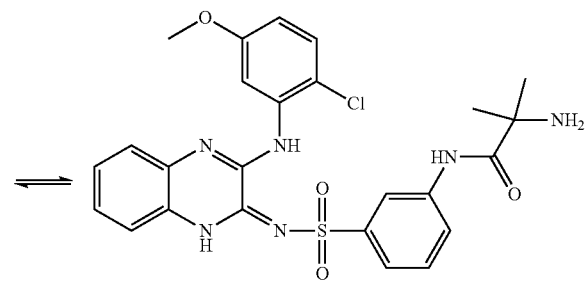

Moreover, intermediates leading to Compounds of Formula I, as well as Compounds of Formula I themselves, can be recovered as uncharged or zwitterionic molecules, or cationic salts such a sodium or potassium, depending on the substitutions on the B ring and on reaction conditions. All such zwitterionic forms are within the scope of the invention, and to the extent that one structure is used to depict a zwitterionic compound, it includes all such zwitterionic forms.

For example, one zwitterionic form of Compound A is Compound A-3

Compound A-3
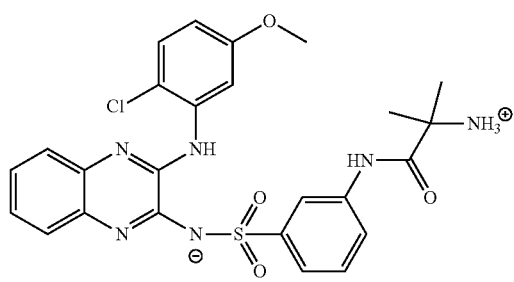
Another zwitterionic depiction of Compound A is Compound A-4.
Compound A-4
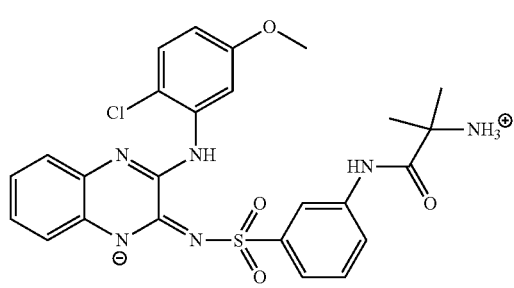
Another zwitterionic depiction of Compound A is Compound A-5.
Compound A-5
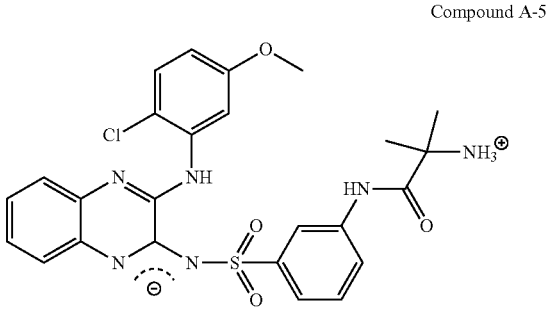 [SMILES: COc1ccc(Cl)c(NC2=Nc3ccccc3NC2NS(=O)(=O)c2cccc(NC(=O)C(C)(C)[NH3+])c2)c1]
As would be understood by a skilled practitioner, tautomeric forms can interconvert.
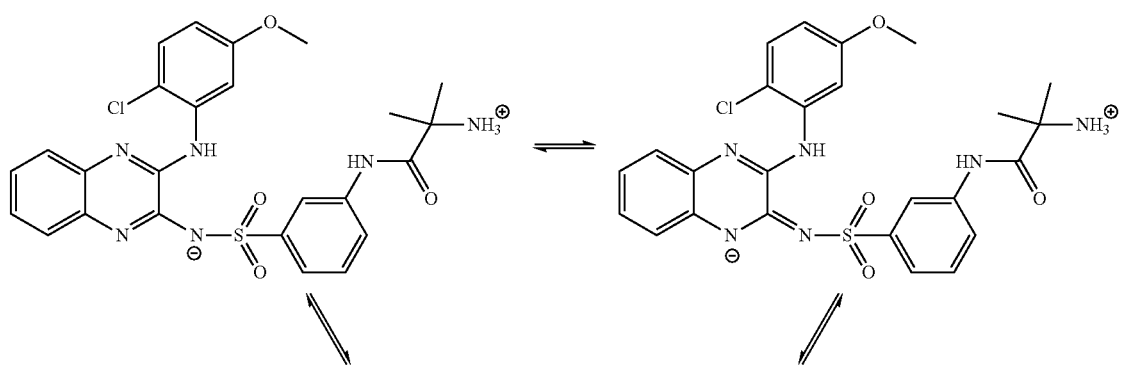
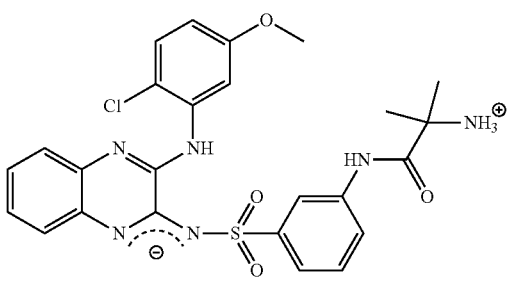

Moreover, interconversion can also exist between the uncharged tautomeric forms and the zwitterionic forms.

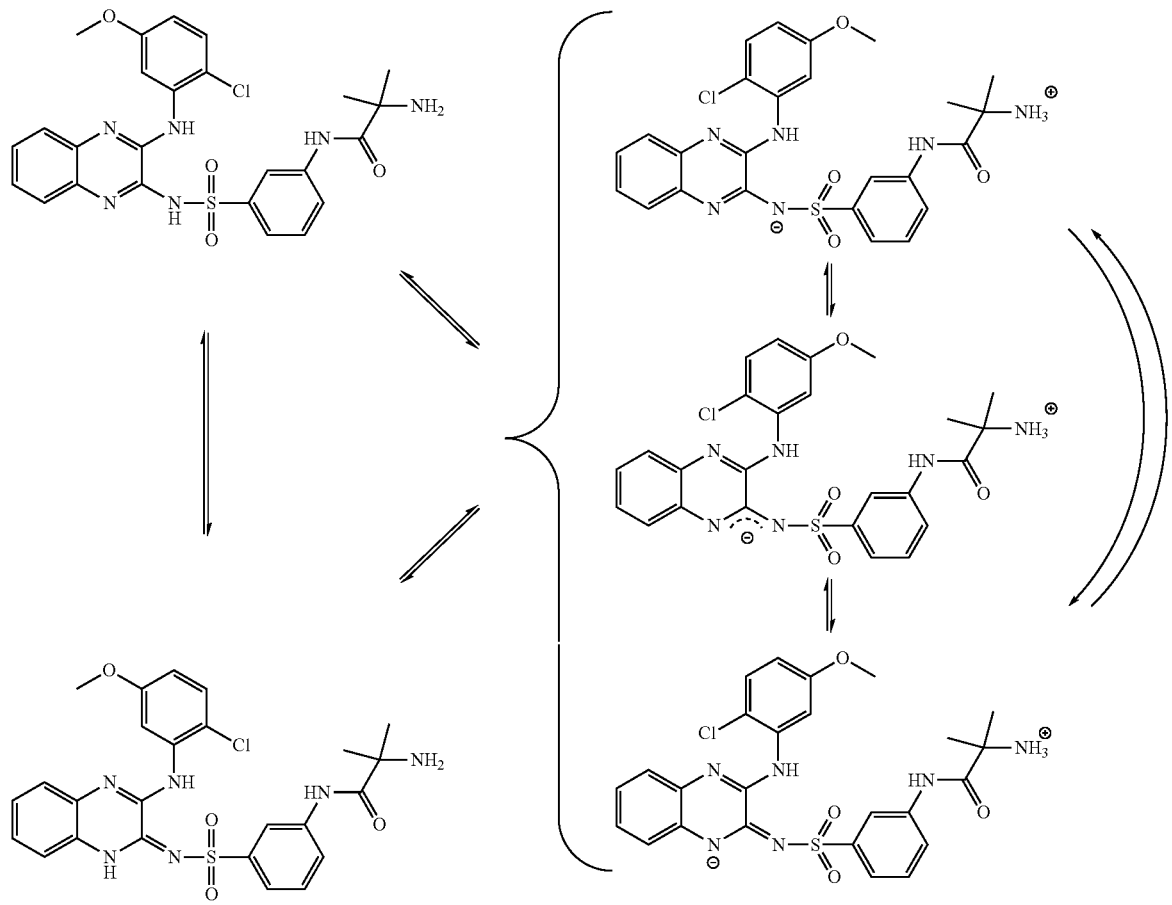 [SMILES: COc1ccc(Cl)c(Nc2nc3ccccc3nc2NS(=O)(=O)c2cccc(NC(=O)C(C)(C)N)c2)c1 ; COc1ccc(Cl)c(Nc2nc3ccccc3nc2[N-]S(=O)(=O)c2cccc(NC(=O)C(C)(C)[NH3+])c2)c1 ; COc1ccc(Cl)c(NC2=Nc3ccccc3NC2NS(=O)(=O)c2cccc(NC(=O)C(C)(C)[NH3+])c2)c1 ; COc1ccc(Cl)c(Nc2nc3ccccc3[nH]/c2=N/S(=O)(=O)c2cccc(NC(=O)C(C)(C)N)c2)c1 ; COc1ccc(Cl)c(Nc2nc3ccccc3[n-]/c2=N/S(=O)(=O)c2cccc(NC(=O)C(C)(C)[NH3+])c2)c1]

Regardless of which structure or which terminology is used, each tautomer or zwitterion is included within the scope of the invention. Thus, as used herein, the structure

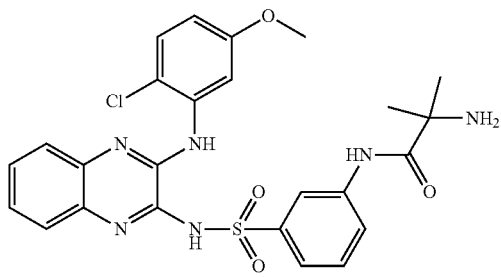 [SMILES: COc1ccc(Cl)c(Nc2nc3ccccc3nc2NS(=O)(=O)c2cccc(NC(=O)C(C)(C)N)c2)c1]

and the associated terms "Compound A" and "N-(3-{[(3-{[2-chloro-5-(methoxy)phenyl]amino}quinoxalin-2-yl)amino]sulfonyl}phenyl)-2-methylalaninamide" encompass all possible tautomeric and zwitterionic forms of the compound.

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. When compounds of Formula I contain groups such as hydroxy, carboxy, thiol or any group containing a nitrogen atom(s), these groups can be protected with a suitable "protecting group" or "protective group." A comprehensive list of suitable protective groups can be found in T. W. Greene, *Protective Groups in Organic Synthesis*, John Wiley & Sons, Inc. 1991, the disclosure of which is incorporated herein by reference in its entirety. The protected derivatives of compounds of Formula I can be prepared by methods well known in the art.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In the examples that follow, unless otherwise specified, the final form of the compound was assumed to be the uncharged molecule in the absence of analytical techniques that would have determined otherwise. Compounds of Formula I can be prepared using methods known to one of ordinary skill in the art or starting from the Compound of formula 1 as depicted in Scheme 1 below. Compounds of formula I can be prepared starting from compound 1 by fusion of appropriate reagents at 180° C. in the presence of a base such as $K_2CO_3$ and metallic copper is known to provide intermediates of formula 1 (see S. H. Dandegaonker and C. K. Mesta, *J. Med. Chem.* 1965, 8, 884).

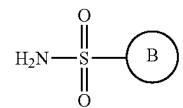

(which are commercially available or can be prepared by one of ordinary skill in the art), a base such as $K_2CO_3$, in a solvent, such as DMF or DMSO. Upon completion (about 2 hours), the reaction mixture is then poured into water and followed by 2 N HCl. The product is then extracted into a solvent such as ethyl acetate and washed with water and brine. The organic layers are combined and dried over a drying agent such as sodium sulfate, filtered, and concentrated under vacuum to provide a compound of formula 3.

The intermediate of formula 3 is then treated with an intermediate of formula 4 in a solvent such as DMF or p-xylene at reflux temperature. Upon completion of the reaction (about 16 hours or less), the reaction is allowed to cool, extracted into DCM, washed with 2 N HCl and brine, dried over a drying agent such as sodium sulfate or magnesium sulfate, filtered, and concentrated to give a compound of Formula I.

Alternatively, other methods to prepare quinoxaline derivatives are known to one skilled in the art and include, but are not limited to S. V. Litvinenko, V. I. Savich, D. D. Bobrovnik, *Chem. Heterocycl. Compd.* (Engl. Transl), 1994, 30, 340 and W. C. Lununa, R. D. Hartman, *J. Med. Chem.* 1981, 24, 93.

Compounds of Formula I where B is phenyl substituted with $R^{3a}$ where $R^{3a}$ is alkylamino or dialkylamino or B is heteroaryl substituted with $R^3$ where $R^3$ is amino, alkylamino, or dialkylamino, and all other groups are as defined in the Summary of the Invention can be prepared according to Scheme 2.

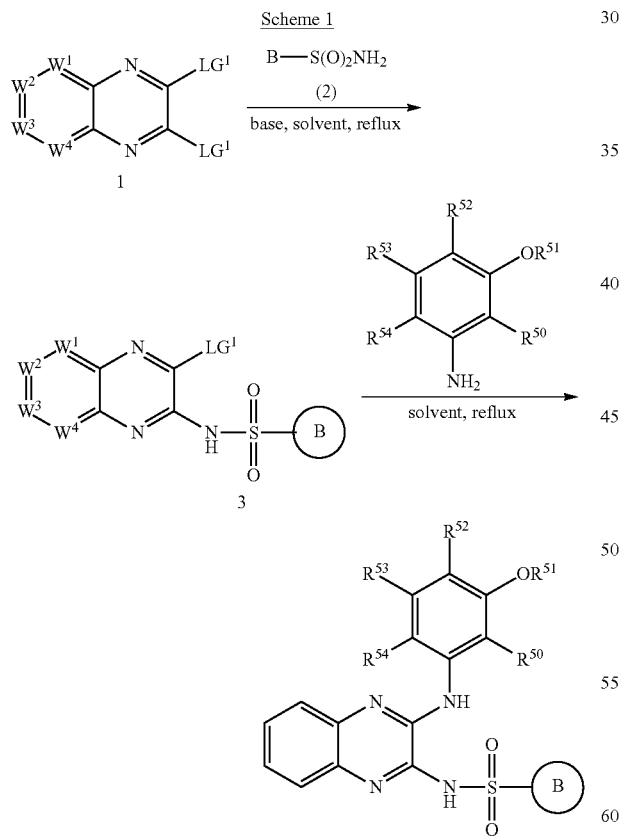

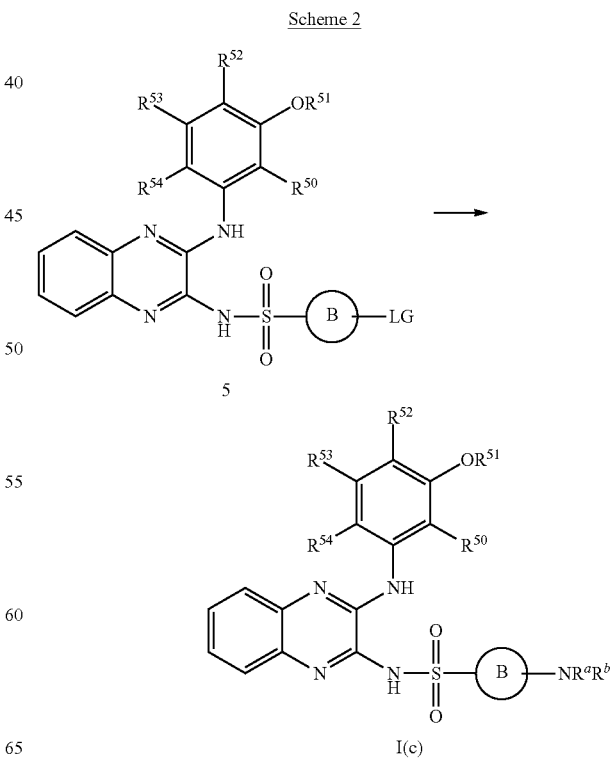

Referring again to Scheme 1, an intermediate of formula 3 can be prepared by briefly heating an appropriately substituted quinoxaline (for example, commercially available 2,3-dichloroquinoxaline) and an appropriately substituted sulfonamide of formula 2

In Scheme 2, LG is a leaving group such as chloro. Compound 5 is reacted with NHR$^a$R$^b$ or HO—C$_1$-C$_6$-alkylene-NHR$^a$R$^b$ where R$^a$ and R$^b$ are independently hydrogen or alkyl. The reaction is carried out in the presence of a base, such as KHCO$_3$, in a solvent such as DMF.

Compounds of Formula I where B is phenyl substituted with R$^{3a}$ where R$^{3a}$ is aminoalkyloxy, alkylaminoalkyloxy, or dialkylaminoalkyloxy or B is heteroaryl substituted with R$^3$ where R$^3$ is aminoalkyloxy, alkylaminoalkyloxy, or dialkylaminoalkyloxy, and all other groups are as defined in the Summary of the Invention can be prepared according to Scheme 3.

Scheme 3

5 ⟶

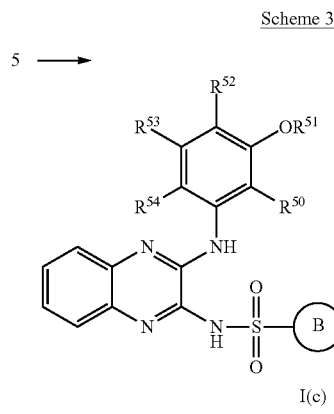

I(c)

The reaction is carried out in the presence of a base such as NaH in a solvent such as DMF.

Compounds of Formula I where B is phenyl substituted with R$^{3a}$ or B is heteroaryl substituted with R$^3$ where R$^{3a}$ and R$^3$ are
  i. —N(R$^7$)C(O)—C$_1$-C$_6$-alkylene-N(R$^{7a}$)(R$^{7b}$) where R$^7$, R$^{7a}$, and R$^{7b}$ are as defined in the Summary of the Invention;
  ii. —NR$^9$C(O)R$^{9a}$ where R$^9$ is as defined in the Summary of the Invention;
  iii. —NR$^{11}$C(O)NR$^{11a}$R$^{11b}$ where R$^{11a}$, R$^{11a}$ and R$^{11b}$ are as defined in the Summary of the Invention;
  iv. —NR$^{13}$C(O)OR$^{13a}$ where R$^{13}$ and R$^{13}$a are as defined in the Summary of the Invention;
  v. —N(R$^{18}$)C(O)—C$_1$-C$_6$-alkylene-N(R$^{18b}$)C(O)R$^{18a}$ where R$^{18}$, R$^{18a}$, and R$^{18b}$ are as defined in the Summary of the Invention;
  vi. —N(R$^{20}$)C(O)—C$_1$-C$_6$-alkylene-C(O)R$^{20a}$ where R$^{20}$ and R$^{20a}$ as defined in the Summary of the Invention;
  vii. —NR$^{21}$S(O)$_2$—C$_1$-C$_6$-alkylene-N(R$^{21b}$)R$^{21a}$ where R$^{21}$, R$^{21a}$, and R$^{21b}$ are as defined in the Summary of the Invention;
  viii. —N(R$^{22}$)C(O)—C$_0$-C$_6$-alkylene-N(R$^{22b}$)—N(R$^{22c}$)(R$^{22a}$), where R$^{22}$, R$^{22a}$ and R$^{22b}$ are as defined in the Summary of the Invention;
  ix. —NR$^{24}$C(O)—C$_1$-C$_6$-alkylene-OR$^{24a}$ where R$^{24}$ and R$^{24a}$ are as defined in the Summary of the Invention;
and where the alkylene in R$^3$ and R$^{3a}$ are independently optionally substituted as described in the Summary of the Invention can be prepared according to Scheme 4 by reacting with an intermediate of formula 9(a), 9(b), 9(c), 9(d), 9(e), 9(f), or 9(g):
  1. 9(a) HOC(O)—C$_1$-C$_6$-alkylene-N(R$^{7a}$)(R$^{7b}$) where R$^a$ is R$^{7a}$ or a N-protecting group, such as Boc or Fmoc;
  2. 9(b) HOC(O)R$^{9a}$;
  3. 9(c) HOC(O)NR$^{11}$ $^a$R$^{11b}$;
  4. 9(d) HOC(O)OR$^{13a}$;
  5. 9(e) HOC(O)—C$_1$-C$_6$-alkylene-N(R$^{18b}$)C(O)R$^{18a}$;
  6. 9(f) HOC(O)—C$_1$-C$_6$-alkylene-C(O)R$^{20a}$;
  7. 9(g) LG-S(O)$_2$—C$_1$-C$_6$-alkylene-N(R$^{21b}$)R$^a$ where R$^a$ is R$^{21a}$ or a N-protecting group, such as Boc or Fmoc.

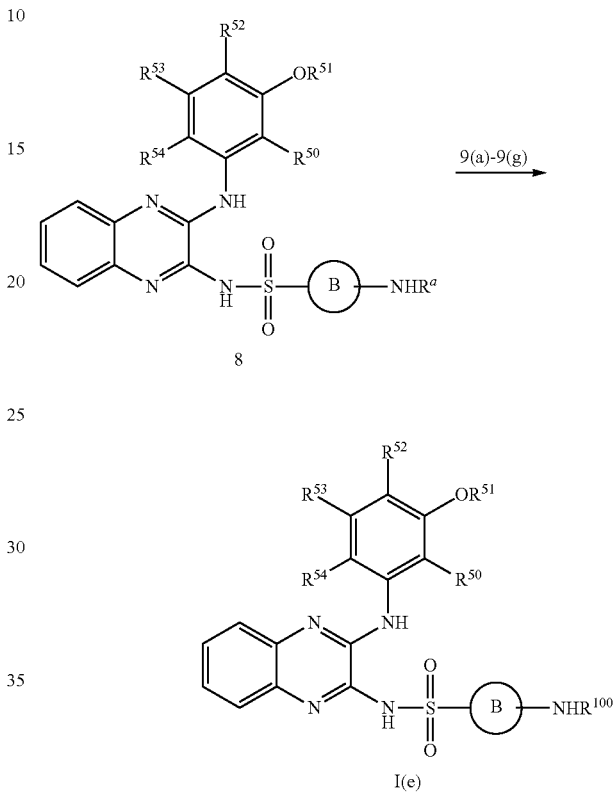

Scheme 4

8

I(e)

In Scheme 4, R$^{100}$ in Scheme 4 is —C(O)R$^{9a}$, —C(O)NR$^{11a}$R$^{11b}$, —C(O)OR$^{13a}$, —C(O)—C$_1$-C$_6$-alkylene-N(R$^{18b}$)C(O)R$^{18a}$, —C(O)—C$_1$-C$_6$-alkylene-C(O)R$^{20a}$, or —S(O)$_2$—C$_1$-C$_6$-alkylene-N(R$^{21b}$)R$^a$. The reaction is carried out under standard amide coupling conditions known to one of ordinary skill in the art. In particular, the reaction is carried out in the presence of a coupling agent such as HATU, a base such as DIEA, and in a solvent such as DMF. Where applicable, the N-protecting group is then removed using procedures known to one of ordinary skill in the art, such as treating with acid where PG is Boc.

Proceeding as described for Scheme 4, compounds of the invention where B is phenyl substituted with R$^{3a}$ or B is heteroaryl substituted with R$^3$ where R$^{3a}$ and R$^3$ are
  i. —C(O)NR$^8$R$^{8a}$;
  ii. —C(O)N(R$^{10}$)—C$_1$-C$_6$-alkylene-N(R$^{10a}$)R$^{10b}$;
  iii. —C(O)R$^{12}$ where R$^{12}$ is an N-substituted heterocycloalkyl;
  iv. —C(O)N(R$^{14}$)N(R$^{14a}$)(R$^{14}$);
  v. —C(O)N(R$^{16}$)—C$_1$-C$_6$-alkylene-C(O)OR$^{16a}$; or
  vi. —C(O)N(R$^{19}$)—C$_1$-C$_6$-alkylene-C(O)R$^{19a}$; or
can be prepared by exchanging the starting materials as necessary. In particular, the intermediate of formula 11:

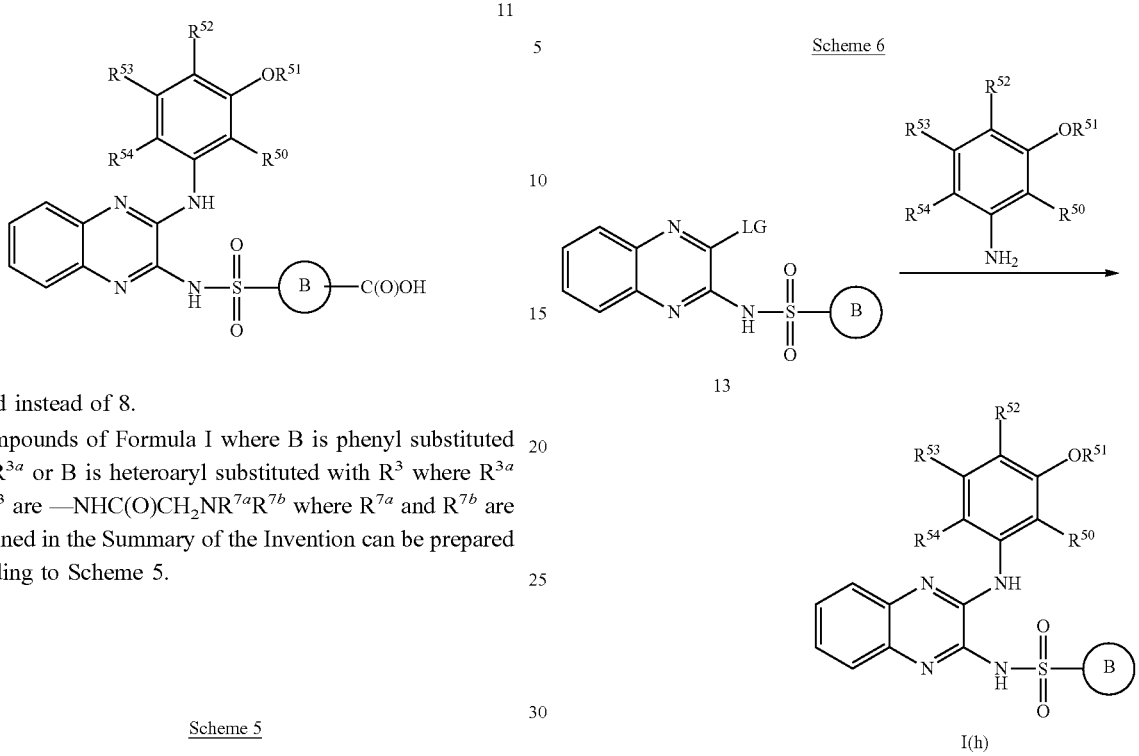

is used instead of 8.

Compounds of Formula I where B is phenyl substituted with $R^{3a}$ or B is heteroaryl substituted with $R^3$ where $R^{3a}$ and $R^3$ are —NHC(O)CH$_2$NR$^{7a}$R$^{7b}$ where $R^{7a}$ and $R^{7b}$ are as defined in the Summary of the Invention can be prepared according to Scheme 5.

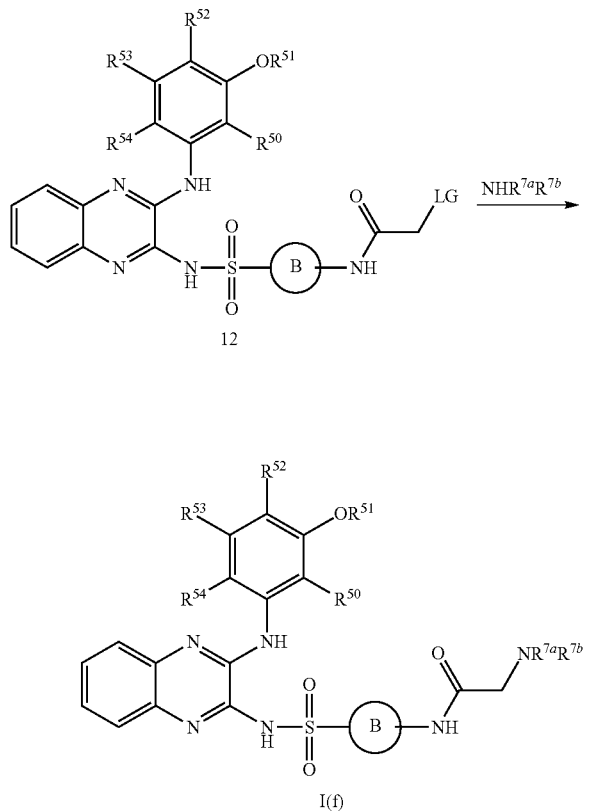

LG is a leaving group such as bronco or chloro. 12 is reacted with NH(R$^{7b}$)R$^{7a}$ in the presence of a base, such as DIEA, in a solvent such as ACN.

Compounds of Formula I can be prepared according to Scheme 6.

Scheme 6

LG in Scheme 6 is a leaving group such as chloro. The reaction can be carried out by irradiating in a solvent such as DMA. Alternatively, the reaction can be carried out in the presence of acetic acid in a solvent such as DMA and by heating.

General Alkylation Procedure 1

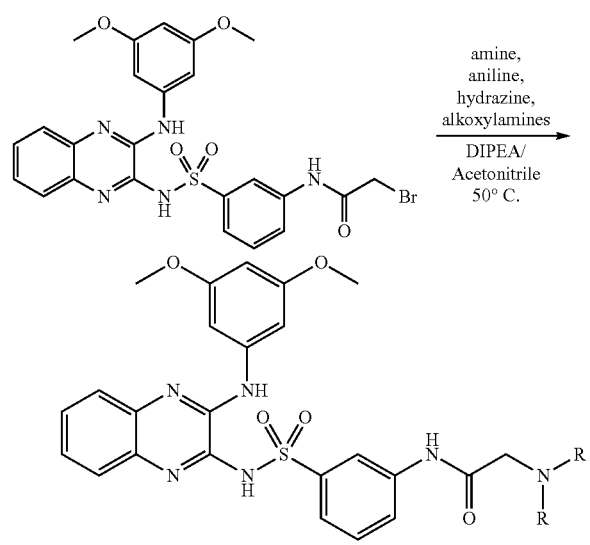

Into a 2-dram vial was placed 2-bromo-N-(3-(N-(3-(3,5-dimethoxy-phenylamino)quinoxalin-2-yl) sulfamoyl)phenyl)acetamide (86 mg, 0.15 mmol), prepared using procedures similar to those in Example 171, along with 2 mL of acetonitrile. Eight equivalents (1.2 mmol) of the desired amine, aniline, hydrazine or alkoxyamine were added followed by the addition of Hunig's Base (41 µL, 0.25 mmol). The reaction then was stirred at 50° C. for one hour (overnight for aniline reagents). Preparative reverse-phase HPLC was used to isolate the desired product directly from the crude reaction mixture. A Waters Fractionlynx preparative reverse-phase HPLC-equipped with a Waters SunFire Prep C18, OCD 5 µM, 30×70 mm column and running a 5-100% gradient with a binary solvent system of 25 mM ammonium acetate in water/acetonitrile—was used to carry out the purification.

General Library Acylation Procedure 1

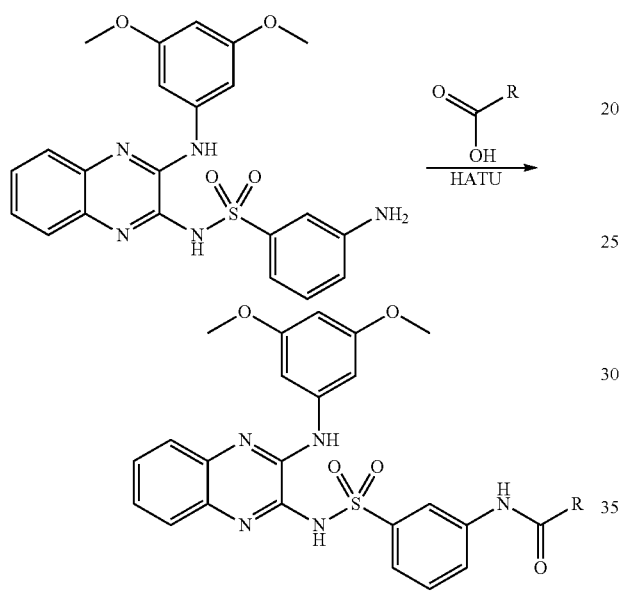

Into a 2-dram vial were added 3-amino-N-(3-(3,5-dimethoxy-phenylamino)quinoxalin-2-yl)benzenesulfonamide (54 mg, 0.12 mmol), prepared using procedures similar to those described in Example 15, DMA (2 mL) and the desired carboxylic acid (0.17 mmol). DIEA (70 µL, 0.4 mmol) followed by HATU (53 mg, 0.14 mmol) were added to the vial and the reaction mixture stirred at 50° C. overnight. Preparative reverse-phase HPLC was used to isolate the desired product directly from the crude reaction mixture. A Waters Fractionlynx preparative reverse-phase HPLC; equipped with a Waters SunFire Prep C18, OCD 5 µM, 30×70 mm column and running a 5-100% gradient with a binary solvent system of 25 mM ammonium acetate in water/acetonitrile; was used to carry out the purification.

General Amination Procedure 1a

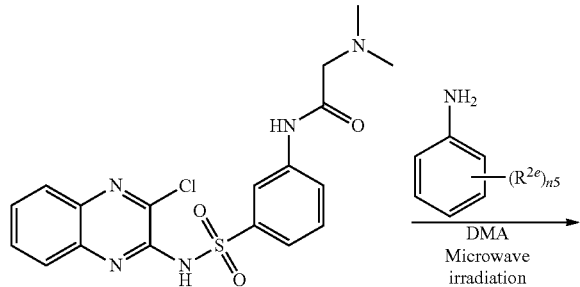

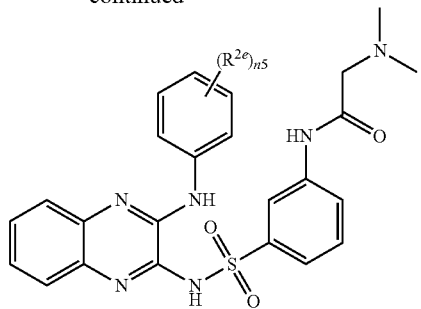

A CEM microwave reaction vessel was charged with N-(3-(N-(3-chloroquinoxalin-2-yl)sulfamoyl)phenyl)-2-(dimethylamino)acetamide (30 mg, 0.071 mmol), prepared using procedures similar to those described in Example 374, the desired aniline (16 mg, 0.14 mmol, 2 eq), and 0.5 mL of dimethylacetamide. The vessel was sealed and the reaction mixture was heated under microwave radiation for 70 min at 140° C. in a CEM Discover microwave instrument. The solvent was then removed by rotary-evaporation. Purification of the final product was accomplished by preparatory reverse-phase HPLC with the eluents 25 mM aqueous NH$_4$OAc/ACN to the desired product.

General Amination Procedure 1b

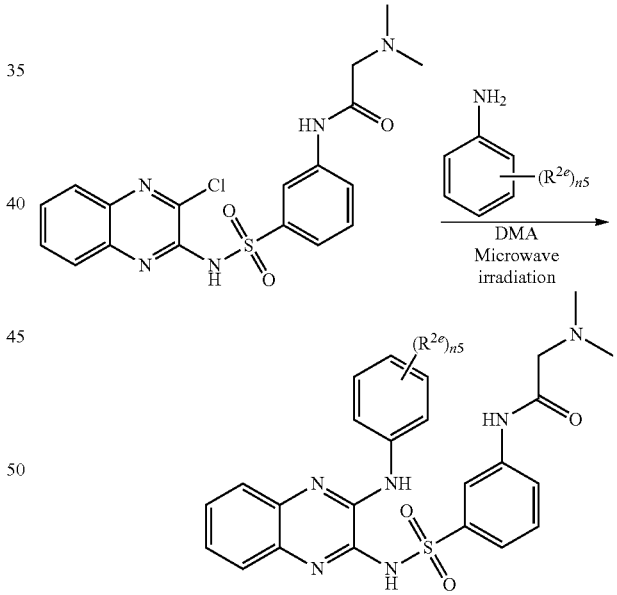

A CEM microwave reaction vessel was charged with N-(3-(N-(3-chloroquinoxalin-2-yl)sulfamoyl)phenyl)-2-(dimethylamino)acetamide (62 mg, 0.147 mmol), prepared using procedures similar to those in Example 374, the desired aniline (0.567 mmol, 4 eq), and 1.0 mL of toluene. The vessel was sealed and the reaction mixture was heated under microwave radiation for 60 min at 180° C. in a CEM Discover microwave instrument. The solvent was removed on a rotary-evaporator. Purification of the final product was done by preparatory HPLC with NH$_4$OAc/ACN as eluent to yield the desired product.

General Acylation Procedure 2

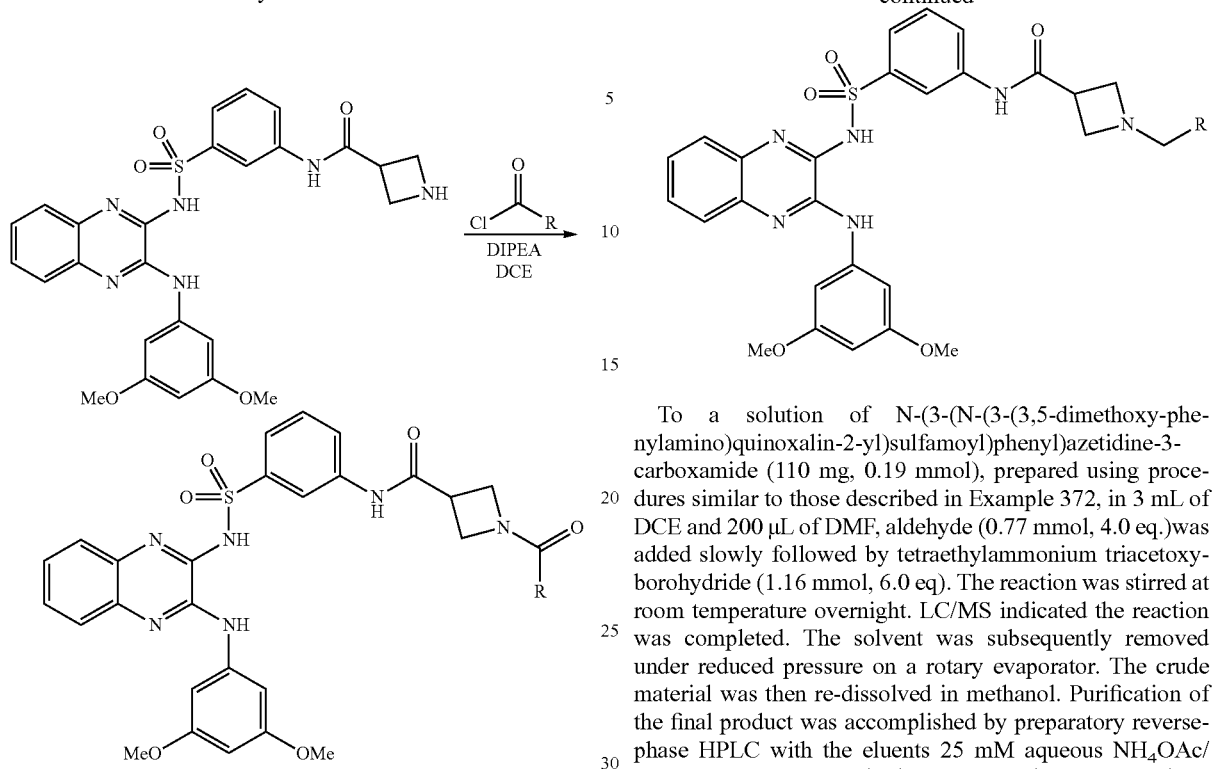

N-(3-(N-(3-(3,5-dimethoxy-phenylamino)quinoxalin-2-yl)-sulfamoyl)phenyl)azetidine-3-carboxamide (125 mg, 0.23 mmol), prepared using procedures similar to those described in Example 372, was dissolved into 5 mL DCE in a 10 mL round-bottom flask. DIEA (1.17 mmol, 5.0 equiv.) was then added with stirring followed by acid chloride (0.47 mmol, 2.0 equiv.). The reaction was then stirred at room temperature for 1 hour or until complete as indicated by LCMS. The solvent was subsequently removed under reduced pressure on a rotary evaporator. The crude material was then re-dissolved in methanol. Purification of the final product was accomplished by preparatory reverse-phase HPLC with the eluents 25 mM aqueous NH4OAc/CAN. A Waters Fractionlynx preparative reverse-phase HPLC; equipped with a Waters SunFire Prep C18, OCD 5 μM, 30×70 mm column and running a 5-100% gradient with a binary solvent system of 25 mM ammonium acetate in water/acetonitrile; was used to carry out the purification.

General Reductive Amination Procedure 1

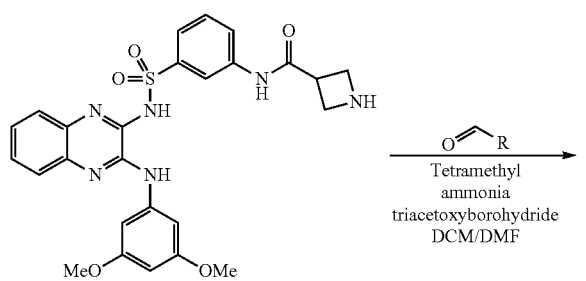

To a solution of N-(3-(N-(3-(3,5-dimethoxy-phenylamino)quinoxalin-2-yl)sulfamoyl)phenyl)azetidine-3-carboxamide (110 mg, 0.19 mmol), prepared using procedures similar to those described in Example 372, in 3 mL of DCE and 200 μL of DMF, aldehyde (0.77 mmol, 4.0 eq.)was added slowly followed by tetraethylammonium triacetoxyborohydride (1.16 mmol, 6.0 eq). The reaction was stirred at room temperature overnight. LC/MS indicated the reaction was completed. The solvent was subsequently removed under reduced pressure on a rotary evaporator. The crude material was then re-dissolved in methanol. Purification of the final product was accomplished by preparatory reverse-phase HPLC with the eluents 25 mM aqueous NH4OAc/CAN. A Waters Fractionlynx preparative reverse-phase HPLC; equipped with a Waters SunFire Prep C18, OCD 5 μM, 30×70 mm column and running a 5-100% gradient with a binary solvent system of 25 mM ammonium acetate in water/acetonitrile; was used to carry out the purification.

General Amide Formation Procedure 1a

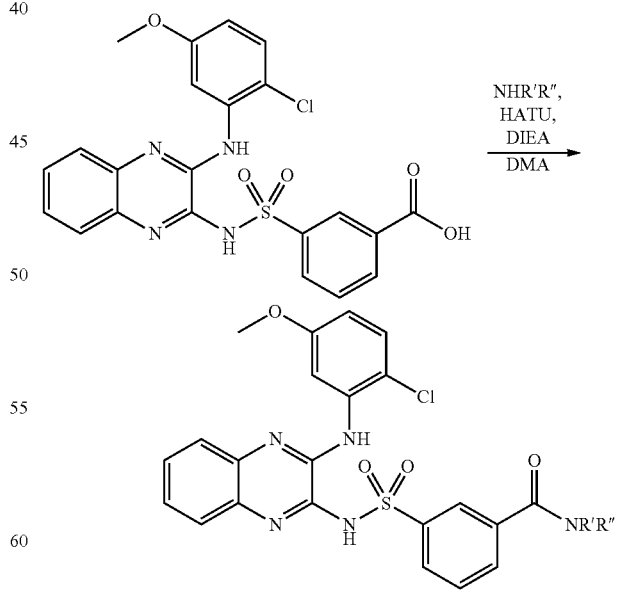

Into a small 1 dram vial was added 3-(N-(3-(2-chloro-5-methoxy-phenylamino)-quinoxalin-2-yl)sulfamoyl)benzoic acid (61 mg, 0.13 mmol, 1.1 equiv), prepared using procedures described for Example 100. The acid was dissolved in DMA (1 mL) and DIEA (42 μL, 0.24 mmol, 2 equiv) was added then added to the solution. The amine reagent (1 mL of 0.12 M solution in DMA) was added to solution with stirring followed by HATU (64 mg, 0.17 mMol, 1.4 equiv). The reaction was stirred overnight at room temperature. Upon completion as indicated by LCMS analysis, 2 mL of methanol was added to the solution. Preparative reverse-phase HPLC was used to isolate the desired product. A Waters Fractionlynx preparative reverse-phase HPLC—equipped with a Waters SunFire Prep C18, OCD 5 μM, 30×70 mm column and running a 5-100% gradient with a binary solvent system of 25 mM ammonium acetate in water/acetonitrile—was used to carry out the purification.

General Amide Formation Procedure 1b

The procedure outlined in General Amide Formation Procedure 1a was used to incorporate a number of amines that contained a second amine group protected as the tert-butylcarbamate (i.e. where R', within NHR'R," contained a Boc-protected amine group). The deprotection was carried out after HPLC purification of the Boc-protected precursor.

Into a small 1 dram vial was added 3-(N-(3-(2-chloro-5-methoxy-phenylamino)quinoxalin-2-yl)sulfamoyl)benzoic acid (61 mg, 0.13 mmol, 1.1 equiv). The acid was dissolved in 1 mL of DMA and DIEA (42 μL, 0.24 mmol, 2 equiv) was added then added to the solution. The mono-Boc-protected diamine reagent (1 mL of 0.12 M solution in DMA, 1 equiv) was added to solution with stirring followed by HATU (64 mg, 0.17 mmol, 1.4 equiv). The reaction was stirred overnight at room temperature. Upon completion as indicated by LCMS analysis, 2 mL of methanol was added to the solution. Preparative reverse-phase HPLC was used to isolate the desired product directly from this crude reaction solution. A Waters Fractionlynx preparative reverse-phase HPLC; equipped with a Waters SunFire Prep C18, OCD 5 μM, 30×70 mm column and running a 5-100% gradient with a binary solvent system of 25 mM ammonium acetate in water/acetonitrile; was used to carry out the purification. The product fractions were combined and concentrated to dryness under reduced pressure by rotary evaporation. A solution of 4 N HCl in dioxane (2 mL) was added. The solution was then stirred at room temperature until no starting material was detected. The deprotected product precipitated out of solution as an HCl salt and was collected by filtration, washed with ether and dried under vacuum.

Synthesis of Compound A

Crude Compound A can be prepared as described below and depicted below in Scheme 7.

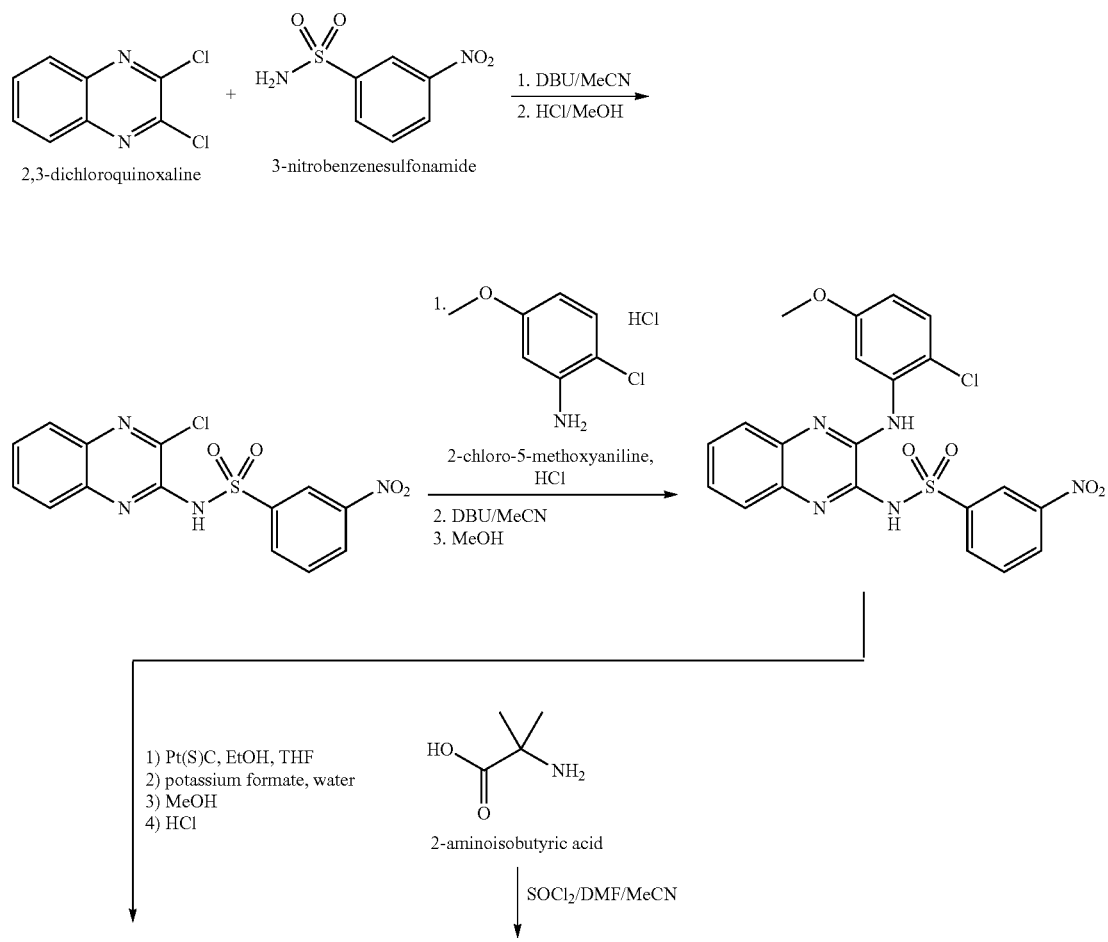

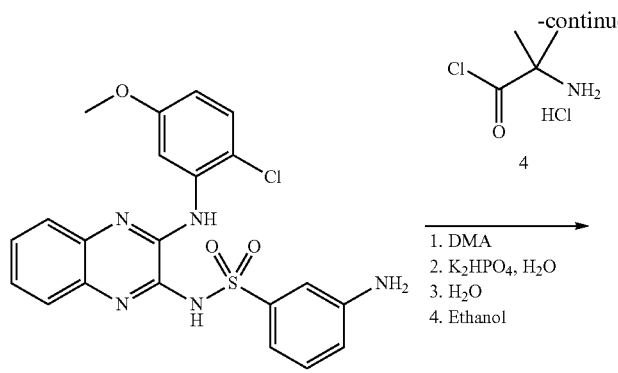
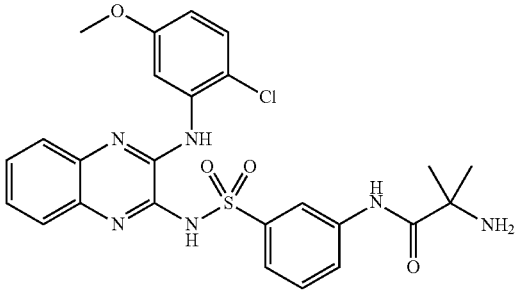

Synthesis of (N-(3-chloroquinoxalin-2-yl)-3-nitrobenzenesulfonamide)

One kg of 2,3 dichloroquinoxaline and one kg of 3-nitrobenzenesulfonamide were mixed in 5 volumes of acetonitrile. The reaction mixture was heated to reflux. 2.3 kg of DBU and 1 volume of acetonitrile were added. After completion of the reaction, the mixture was cooled down at 5° C. Twelve volumes of methanol and 1.53 kg of HCl were added, and the reaction mixture was filtered. The filter cake was washed with 6 volumes of methanol and dry under vacuum.

Synthesis of (N-(3-((2-chloro-5-methoxyphenyl)amino)quinoxalin-2-yl)-3-nitrobenzenesulfonamide)

A solution was prepared with 0.585 kg of 2-chloro-5-methoxyaniline-HCl, 3.5 volumes of acetonitrile and 0.46 kg of DBU (solution A). Separately, 1 kg of N-(3-chloroquinoxalin-2-yl)-3-nitrobenzenesulfonamide and 5.5 volumes of acetonitrile were combined and heated to reflux. Solution A and 1 volume of acetonitrile were then added to the reaction mixture, and the resulting mixture was heated at reflux. After completion of the reaction, the mixture was cooled down at 20° C., diluted with 10 volumes of methanol and filtered. The resulting filter cake was washed 3 times with 5 volumes of methanol and then dried under vacuum.

Synthesis of 3-amino-N-{3-[(2-chloro-5-methoxyphenyl)amino]quinoxalin-2-yl}benzenesulfonamide hydrochloride To 1 kg of N-{3-[(2-chloro-5-methoxyphenyl)amino]quinoxalin-2-yl}-3-nitrobenzenesulfonamide was added a catalytic amount of platinum sulfide on carbon (Pt(S)C), 6 volumes of THF, 0.16 volume of water, and 2 volumes of ethanol. The resulting reaction mixture was stirred and heated to reflux. An aqueous potassium formate solution (1.4 volume of water+0.69 kg of potassium formate) was added. The reaction mixture was stirred at reflux until completion of the reaction and then cooled down at 50° C. After the addition of 10 volumes of methanol and one hour of stirring, the catalyst was filtered off and washed with 3.4 volumes of methanol. The filtered solution was cooled down at 20° C. and 0.62 kg of HCl was added. The reaction mixture was stirred at 20° C., cooled down to 5° C. and filtered. The filter cake was washed with methanol (6 volumes) and dried under vacuum.

Synthesis of N-[3-({3-[(2-chloro-5-methoxyphenyl)amino]quinoxalin-2-yl}sulfamoyl)phenyl]-2-methylalaninamide (Crude)

Synthesis of 2-methylalanyl chloride hydrochloride. To 0.42 kg of 2-amino-2-methylpropanoic acid, was added 3.7 volumes of acetonitrile, 0.04 volume of dimethylformamide, and 0.62 kg of oxalyl chloride. The reaction mixture was stirred at 20° C. until completion of the reaction. The mixture was then filtered, and the filter cake was washed twice with 1 volume of acetonitrile and dried under vacuum.

To 1 kg of 3-amino-N-{3-[(2-chloro-5-methoxyphenyl)amino]quinoxalin-2-yl}benzenesulfonamide hydrochloride was added 8 volumes of dimethylformamide and 0.385 kg of 2-methylalanyl chloride hydrochloride at 5° C. After completion of the reaction, the mixture was heated to 50° C. and a solution of K2HPO4 (1.4 kg), water (16.5 volumes) and ethanol (7.1 volumes) was added. The mixture was cooled down to 10° C., stirred 2 hours at 10° C., and then filtered. The cake was washed 3 times with 10 volumes of water and dried under vacuum.

EXAMPLE 1

Phase I Trial of Compound A, a Pan-Phosphatidylinositol 3 Kinase (PI3K) Inhibitor, in Patients with Chronic Lymphocytic Leukemia (CLL) and Lymphoma Dysregulation of the class I phosphatidylinositol 3-kinases (PI3Ks) have been implicated in cancer pathogenesis in many cell types, and the PI3K pathway is constitutively activated in CLL and often in other non-Hodgkin lymphomas.

Compound A is a potent and selective inhibitor of all four class I PI3K isoforms, with IC50s (nM) of α:39, β:383, γ:36, and δ:23, compared to mTOR:>15000. In preclinical xenograft model studies, Compound A inhibited phosphorylation of downstream effectors of PI3K and inhibited tumor growth at well-tolerated doses. In vitro and in vivo, Compound 1 inhibits phosphorylation of downstream targets of PI3K, including pAKT and pEBP1.

As part of a phase 1 single agent study in solid tumors, we administered Compound A to a dedicated expansion cohort of patients with relapsed/refractory lymphoma and CLL. The drug was administered orally daily, with continuous dosing in monthly cycles. A total of 15 patients were enrolled at three centers. An initial cohort of 3 patients was enrolled, followed by a safety review, with subsequent enrollment of the remaining 12 subjects. The median age of the patients was 66 years (range 28-81), 40% were male and 60% female.

Among the 15 patients, 33% (n=5) had refractory CLL, and 67% (n=10) had various relapsed lymphomas, including diffuse large B-cell lymphoma (DLBCL) (n=4), follicular lymphoma (n=2), Hodgkin lymphoma (n=2), Waldenstrom's macroglobulinemia (n=1), and B-cell prolymphocytic leukemia (n=1). 93% (n=14) had stage 3-4 disease. Among 12 patients with data available, 6 (50%) had received 3 or more prior therapies, 10 (83%) had been exposed rituximab, and 11 (92%) to alkylating agents. Overall, the median hemoglobin was 11.3 g/dL (range 9.2-14.1), and the median platelet count was $113 \times 10^3/\mu l$ (range 31-470). For the 5 patients with CLL, the median starting absolute lymphocyte count(ALC) was $1.9 \times 10^3/\mu l$ (range 0.9-22.8); the median starting hemoglobin was 10.8 g/dL (range 9.2-14.1) and the median platelet count was $83 \times 10^3/\mu l$ (range 66-143). Two CLL patients had 11q deletion and one had 17p deletion. Two of 4 CLL patients tested for IgVH status were unmutated, and two of 2 tested for ZAP70 were positive. Four of 5 patients with CLL had been treated with fludarabine combination chemotherapy.

The median number of treatment cycles of Compound A delivered on study was 4, with 8 patients currently continuing on treatment. Causes of study discontinuation included disease progression (n=6) and a serious adverse event (n=1 with recurrent hospitalization for pneumonia). Adverse events were infrequent, and those of any grade occurring in >10% of patients included diarrhea, hyperglycemia, headache, and lymphopenia. Hematologic toxicity was uncommon, with grade 3-4 neutropenia in 4/15 (26.7%), and grade 3-4 thrombocytopenia in 1/15 (6.7%). Hyperglycemia was not a significant clinical problem, with 1 (6.7%) grade 3-4 event and 1 (6.7%) grade 1-2 event. Patients are being followed for response and updated data will be presented. Analysis of pharmacokinetic and pharmacodynamic data, as well as potential predictive biomarkers, is ongoing.

Compound A administered once daily inhibited PI3K pathway activation in surrogate tissue (PBMC, hair follicle, skin) and tumor tissue from patients with solid tumors. Compound A produced robust PI3K and ERK pathway inhibition at well-tolerated doses, and its effect as monotherapy was found to be primarily anti-proliferative, not pro-apoptotic. The maximum tolerated dose (MTD) was defined as 600 mg (capsule) once daily (QD) on either a 21/7 (administered continuously for 21 days followed by 7 days rest) or a continuous daily dosing schedule. Dose-limiting toxicities were Grade 3 rash and Grade 3 hypersensitivity. A dose-escalation study of a tablet formulation is ongoing. Ten additional patients have been enrolled in the expansion cohort to better define the activity of Compound A, and further studies are warranted.

The safety and the pharmacokinetics of 600 mg of Compound A administered as a continuous daily dosing regimen to a dedicated expansion cohort of a phase 1 trial in patients with relapsed/refractory lymphoma and chronic lymphocytic leukemia (CLL) is described herein.

Patients and Methods
  Study Design
  This was a Phase 1, open-label, non-randomized trial of Compound A given orally as a single agent in subjects with lymphoma.
  Objectives
  The primary objective was to determine the safety and tolerability of Compound A administered orally as a 600 mg capsule in subjects with lymphoma.

The secondary objectives were to determine (a) the plasma pharmacokinetics of Compound A; and (b) the pharmacodynamic effects of Compound A on tumor tissue.

The exploratory objectives were to determine the pharmacodynamic effects of Compound A in subjects with lymphoma.

Key Eligibility Criteria

The key eligibility include the following:

Histologically confirmed diagnosis of relapsed or refractory lymphoma

Measureable disease

Adequate bone marrow function defined as:
  $ANC \geq 1000/mm^3$ (CLL with $ALC \geq 100,000/mm^3$ required to have $ANC \geq 500/mm^3$)
  $Platelets \geq 30,000/mm^3$
  $Hemoglobin \geq 8$ g/dL Archival or fresh tumor tissue No prior therapy with a selective PI3K inhibitor Written informed consent.

Results

A total of twenty-five patients were enrolled in the lymphoma cohort. The preliminary data is presented as of the cut-off date of Sep. 1, 2011. Baseline characteristics of the patients are presented in Table 1.

TABLE 1

| Characteristic | N = 19 | |
| --- | --- | --- |
| Age in years, median (range) | 66 (28-83) | |
| Sex, n(%) | | |
| Male | 8 (42) | |
| Female | 11 (58) | |
| Tumor Type, n (%) | | |
| CLL/SLL | 7 (37) | |
| Diffuse large B-cell lymphoma | 4 (21) | |
| Follicular Lymphoma Grade 1-2 | 2 (11) | |
| Follicular Lymphoma Grade 3 | 1 (5) | |
| Waldenstrom's Macroglobulinemia | 1 (5) | |
| Hodgkin Lymphoma | 2 (11) | |
| Transformed lymphoma | 1 (5) | |
| Stage, n (%) | | |
| I | 1 (5) | |
| II | 1 (5) | |
| III | 3 (16) | |
| IV | 10 (53) | |
| Missing | 4 (21) | |
| ECOG performance status, n (%) | | |
| 0 | 5 (27) | |
| 1 | 13 (68) | |
| 2 | 1 (5) | |
| Number of prior therapies within 5 years, median (range) | 3 (1-9) | |
| Hematologic Parameters | CLL/SLL | Non CLL/SLL |
| Absolute lymphocyte count (109) | 1.9 (0.4-37.2) | 0.7 (0.3-23.1) |
| Hemoglobin (g/dL) | 108 (92-141) | 114 (93-150) |
| Platelet Count (109) | 87 (66-187) | 125 (82-470) |

The most common adverse events experienced among the nineteen test subjects are summarized in Table 2.

TABLE 2

| Adverse Event[b] | All Adverse Events | | Related Adverse Events[a] | |
|---|---|---|---|---|
| | All Grades | Grade ≥3[c] | All Grades | Grade ≥3[c] |
| Hematologic | | | | |
| Neutropenia | 5 (26) | 5 (26) | 4 (21) | 4 (21) |
| Anemia | 4 (21) | 3 (16) | 1 (5) | 0 |
| Non-Hematologic | | | | |
| Diarrhea | 12 (63) | 1 (5) | 7 (37) | 1 (5) |
| Cough | 6 (32) | 1 (5) | 0 | 0 |
| Pyrexia | 5 (26) | 1 (5) | 1 (5) | 0 |
| Fatigue | 5 (26) | 0 | 0 | 0 |
| Abdominal Pain | 4 (21) | 1 (5) | 2 (11) | 0 |
| Dyspnea | 4 (21) | 1 (5) | 0 | 0 |
| Hyperglycemia | 4 (21) | 1 (5) | 4 (21) | 1 (5) |
| Pruritus | 4 (21) | 1 (5) | 2 (11) | 0 |
| Rash | 4 (21) | 1 (5) | 3 (16) | 1 (5) |

[a]Adverse events related to the study treatment Compound A combined with paclitaxel and carboplatin
[b]MedDRA v. 12.1 Preferred Terms (converted to US spelling)
[c]NCI-CTCAE v. 3.0 grading Study treatment details for the nineteen subjects are summarized in Table 3.

TABLE 3

| | |
|---|---|
| Median duration of treatment, weeks (range)* | 16 (2-48) |
| Chronic lymphocytic leukemia (n = 7) | 20 (9-29) |
| Diffuse-large B-cell lymphoma (n = 4) | 6 (2-18) |
| Other (n = 7) | 16 (4-48) |
| Patients requiring dose modification due to toxicity†, n (%) | 7 (37) |
| Hyperglycemia | 1 (5) |
| Neutropenia | 2 (11) |
| Rash | 1 (5) |
| Fever/hypotension‡ | 1 (5) |
| Respiratory infection‡ | 1 (5) |
| More than 1 event in the same patient | 1 (5) |
| Diarrhea | |
| Fever/pneumonia | |
| Fever/pneumonia/sepsis/ileus/fluid overload‡ | |
| Discontinuation of treatment, n (%) | |
| Disease progression | 8 (42) |
| Investigator discretion | 1 (5) |

*Data not available for one patient
†One event per patient unless stated otherwise
‡Unrelated to study drug Table 4 summarizes the best response in patients evaluated for efficacy (N=11)[a].

TABLE 4

| Malignancy | n | Complete Response | Partial Response | Stable Disease | Progressive Disease |
|---|---|---|---|---|---|
| CLL/SLL | 5 | | | 5[b] | |
| Follicular Lymphoma | 2 | | | 2 | |
| Waldenstrom's Macroglobulinemia | 1 | 1[c] | | | |
| Transformed Lymphoma | 1 | | | 1[d] | |
| Hodgkin Lymphoma | 2 | | | 1[e] | 1 |

CLL, chronic lymphocytic leukemia; SLL, small lymphocytic lymphoma
[a]Patients with disease assessments after cycle 2 (8 weeks) of Compound 1 600 mg capsule once daily. Responses were assessed by the investigators.
[b]Three patients had a nodal response (decreased lymphadenopathy and increased lymphocytosis) and remain on treatment (n = 2 in cycle 11 and n = 1 in cycle 6); one patient with stable disease (<50% reduction in adenopathy and persistent lymphocytosis) is currently in cycle 7.
[c]Complete response at cycle 14 and remains on treatment
[d]Stable disease currently in cycle 9
[e]Stable disease currently in cycle 10

FIG. 1 depicts the plasma pharmacokinetics observed for Compound A. The mean (SD plasma concentration of Compound A in cycle 1, on Days 1 and 28 after 600 mg Compound A oral doses.) FIG. 1 indicates that drug exposure in the lymphoma patients who were enrolled in the study was similar to that seen previously in patients with solid tumors after 600 mg daily doses. The mean (CV %) accumulation (AUC) on day 28 was approximately 11.2-fold (88.1%), in eight patients. There was inter-patient variability, and the geometric mean was 7.6 fold.

The results demonstrate that Compound A is well-tolerated in patients with lymphoma and CLL and is active in CLL and low-grade lymphomas. The observed pharmacokinetic profile is similar to that seen in patients with solid tumors.

The foregoing invention has been described in some detail by way of illustration and example, for purposes of clarity and understanding. The invention has been described with reference to various specific embodiments and techniques. However, it should be understood that many variations and modifications may be made while remaining within the spirit and scope of the invention. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

What is claimed is:

1. A method of treating a lymphoproliferative malignancy in a human patient in need of such treatment, comprising administering to the patient an effective amount of Compound A

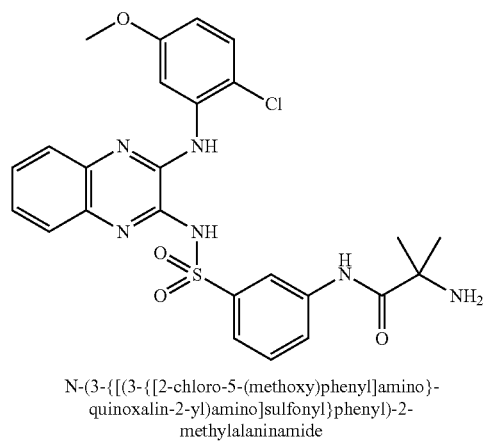 [SMILES: COc1ccc(Cl)c(Nc2nc3ccccc3nc2NS(=O)(=O)c2cccc(NC(=O)C(C)(C)N)c2)c1]

N-(3-{[(3-{[2-chloro-5-(methoxy)phenyl]amino}-quinoxalin-2-yl)amino]sulfonyl}phenyl)-2-methylalaninamide or a pharmaceutically acceptable salt thereof, wherein the Compound A or pharmaceutically acceptable salt thereof is administered at a continuous once daily dose in capsule form of about 600 mg or at a continuous once daily dose in tablet form of about 200 to about 600 mg, and wherein the lymphoproliferative malignancy is relapsed or refractory.

2. The method of claim 1, wherein the Compound A or pharmaceutically acceptable salt thereof is administered at a continuous once daily dose in tablet form of about 400 mg.

3. The method of claim 1, wherein the patient fasts prior to the administration.

4. The method of claim 1, wherein the lymphoproliferative malignancy is chronic lymphocytic leukemia/small lymphocytic lymphoma, Hodgkin's lymphoma, Waldenstrom's macroglobulinemia, follicular lymphoma, or diffuse large B-cell lymphoma or transformed lymphoma.

5. The method of claim 1, wherein the effective amount produces at least one therapeutic effect selected from the group consisting of reduction in size of a tumor, reduction in metastasis, complete remission, partial remission, stable disease, increase in overall response rate, or a pathologic complete response.

* * * * *